(12) United States Patent
Kajiwara et al.

(10) Patent No.: US 7,377,701 B2
(45) Date of Patent: May 27, 2008

(54) RADIATION IMAGING APPARATUS AND LARGE-AREA FIBER PLATE

(75) Inventors: Kenji Kajiwara, Kanagawa (JP); Osamu Hamamoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/767,347

(22) Filed: Jun. 22, 2007

(65) Prior Publication Data

US 2007/0248306 A1    Oct. 25, 2007

Related U.S. Application Data

(62) Division of application No. 11/603,575, filed on Nov. 22, 2006, which is a division of application No. 10/888,175, filed on Jul. 9, 2004, now abandoned, which is a division of application No. 09/922,641, filed on Aug. 7, 2001, now Pat. No. 6,800,857.

(30) Foreign Application Priority Data

| Aug. 10, 2000 | (JP) | ............................. 2000/243180 |
| Aug. 10, 2000 | (JP) | ............................. 2000/243181 |
| Aug. 10, 2000 | (JP) | ............................. 2000/243182 |
| Aug. 10, 2000 | (JP) | ............................. 2000/243183 |
| Aug. 10, 2000 | (JP) | ............................. 2000/243184 |
| Aug. 10, 2000 | (JP) | ............................. 2000/243185 |
| Aug. 10, 2000 | (JP) | ............................. 2000/243186 |

(51) Int. Cl.
*G02B 6/04* (2006.01)

(52) U.S. Cl. ........................... 385/89; 385/88; 385/120

(58) Field of Classification Search .................. 385/14, 385/120, 88, 89
See application file for complete search history.

(56) References Cited

U.S. PATENT DOCUMENTS

| 5,528,719 A | 6/1996 | Yamada ....................... 385/137 |
| 5,563,414 A | 10/1996 | Sklebitz ....................... 250/368 |
| 5,715,292 A | 2/1998 | Sayag et al. ................. 250/368 |
| 5,834,782 A | 11/1998 | Schick et al. .......... 250/370.11 |
| 2002/0005489 A1 | 1/2002 | Kasuyama et al. ......... 250/368 |
| 2007/0081776 A1* | 4/2007 | Kajiwara et al. ........... 385/120 |

FOREIGN PATENT DOCUMENTS

| EP | 1148349 | 10/2001 |
| WO | WO-0036436 A1 | 6/2000 |

* cited by examiner

*Primary Examiner*—Kevin S Wood
(74) *Attorney, Agent, or Firm*—Fitzpatrick, Cella, Harper & Scinto

(57) ABSTRACT

The invention provides a fiber plate formed by arranging in mutually adjacent manner plural individual fiber plates of a same thickness so as to provide a light guiding plane larger in area than the light guiding plane of the individual one fiber plate, and a radiation image pickup apparatus utilizing such fiber plate, in which:

each of the plural individual fiber plates is composed of a group of optical fibers having mutually parallel axes, and lateral faces of the plural individual fiber plates are mutually so bonded that the axes of the optical fibers thereof become mutually parallel.

14 Claims, 30 Drawing Sheets

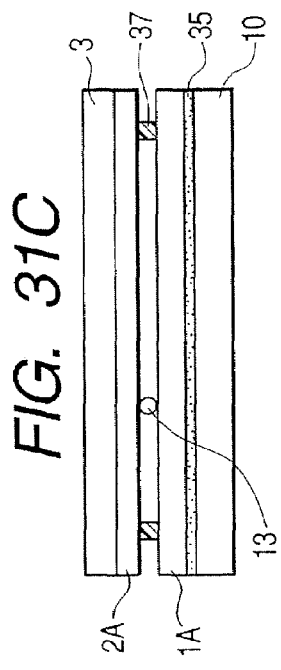
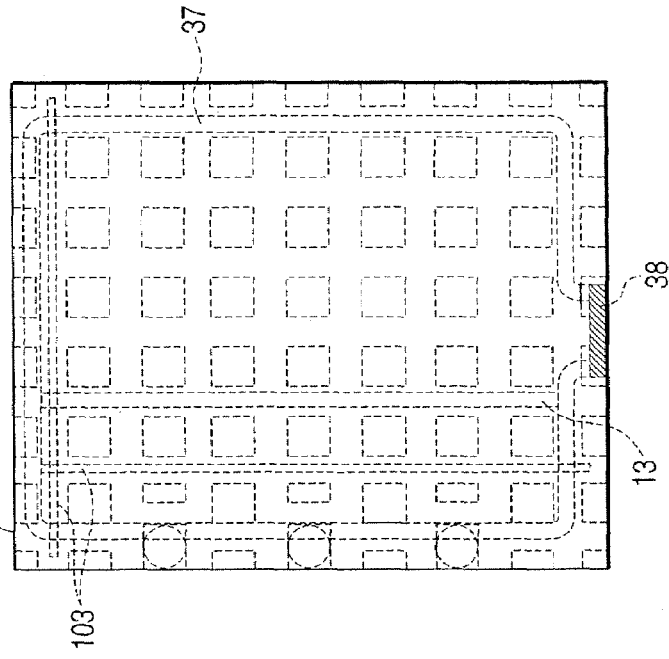
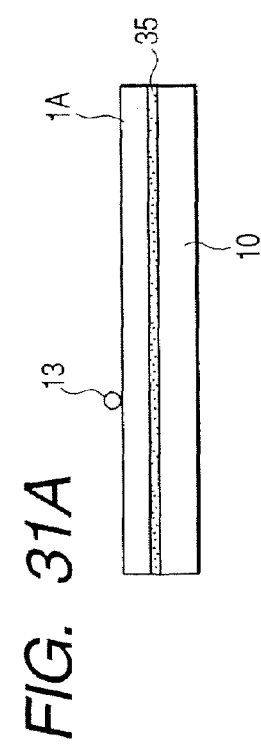
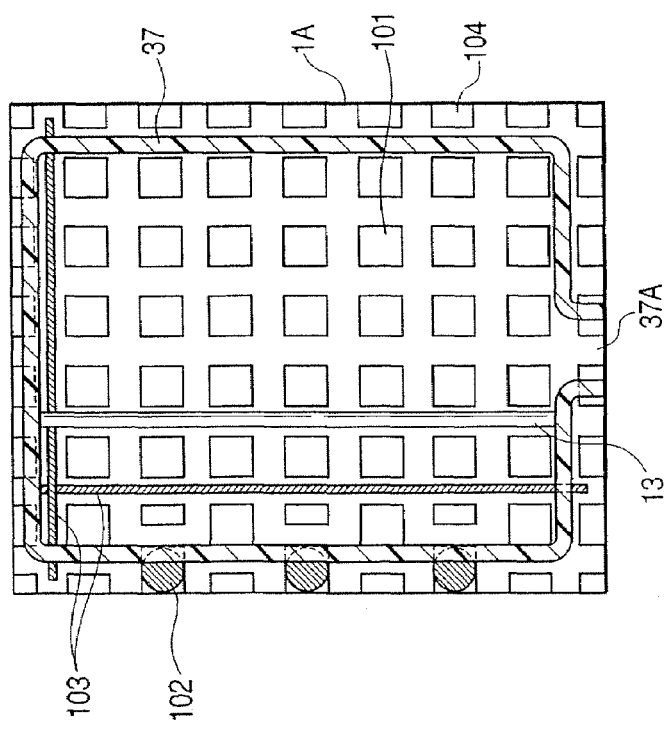

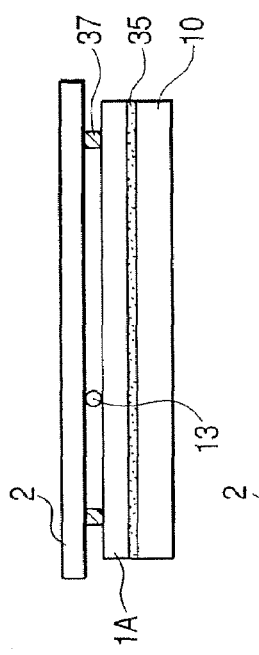
FIG. 32A
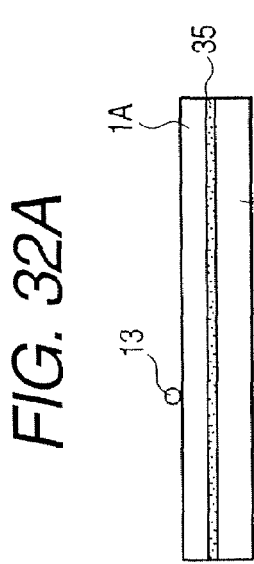
FIG. 32B
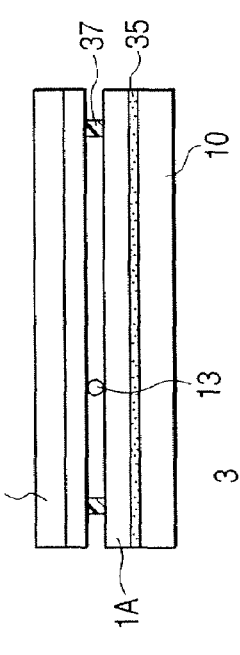
FIG. 32C
FIG. 32D
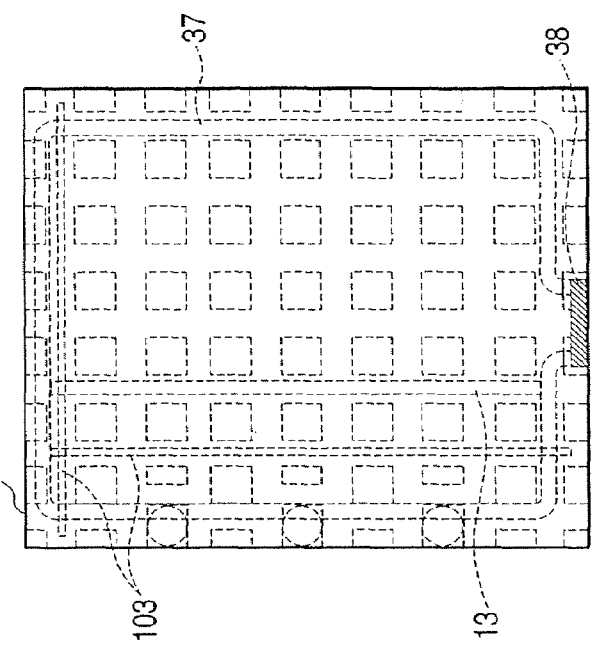
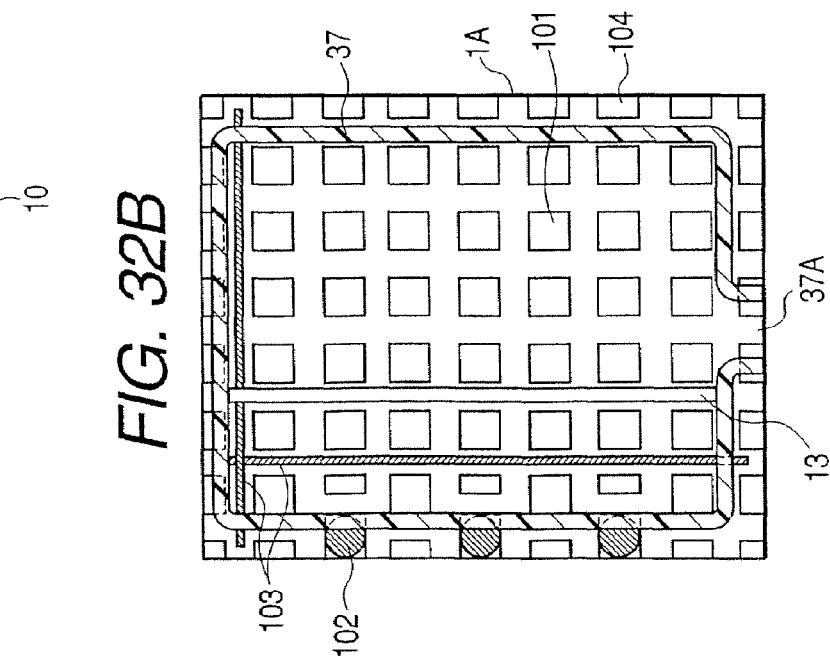
FIG. 32E

RADIATION IMAGING APPARATUS AND LARGE-AREA FIBER PLATE

This application is a division of application Ser. No. 11/603,575 filed Nov. 22, 2006, which was a division of application Ser. No. 10/888,175, filed Jul. 9, 2004, now abandoned, which was a division of application Ser. No. 09/922,641, filed Aug. 7, 2001 now issued as U.S. Pat. No. 6,800,857.

BACKGROUND OF THE INVENTION

Field of the Invention

The present invention relates to a fiber plate (also called fiber optic plate), a radiation image pickup apparatus, a producing method therefore and a radiation image pickup system provided with the same, and more particularly to a fiber plate adapted for use in a radiation image pickup apparatus provided with conversion means for converting a radiation into light and a photoelectric converting element for converting light into an electrical signal and adapted to guide the light from the conversion means to the photoelectric converting element.

In the field of radiation image pickup apparatus, particularly of X-ray image pickup apparatus for medical purpose, there has been desired an X-ray image pickup apparatus of thin type, having a large image input area and capable of taking X-ray moving image with a high image quality. Also for the non-destructive testing apparatus for industrial use, there is required a thin and inexpensive X-ray image of a large area.

For such X-ray image pickup apparatus, there are proposed, for example, (1) an X-ray detecting apparatus having a fiber plate of which the fibers are inclined to prevent mutual interference of the non-light receiving areas of a CCD sensor thereby achieving a large area (as disclosed in the U.S. Pat. No. 5,563,414, and (2) an X-ray detecting apparatus having a fiber plate of which thickness is given a step difference to prevent mutual interference of the non-light receiving areas of a CCD sensor thereby achieving a large area (as disclosed in the U.S. Pat. No. 5,834,782).

FIG. 37 is a schematic cross-sectional view of an X-ray detecting apparatus of the above-mentioned configuration (1), composed of a phosphor 3 consisting for example of a scintillator for converting X-ray into visible light, individual fiber plates 2A consisting of optical fibers or the like for guiding the visible light, obtained by the phosphor 3, to an image pickup element 1, and an image pickup element 1A for converting the visible light, guided by the individual fiber plates 2A, into an electrical signal.

In this X-ray image pickup apparatus, the individual fiber plate 2A is inclined with respect to the image pickup element 1A, and, between the individual fiber plates 2A, there is provided a process circuit or the like for processing the electrical signal from each image pickup element 1A.

FIG. 38 is a schematic perspective view of an X-ray detecting apparatus of the above-mentioned configuration (2), wherein components equivalent to those in FIG. 37 are represented by corresponding numbers. As shown in FIG. 38, the length of the fiber plate 2 is partially changed and for example three image pickup elements are provided as a set with step differences therebetween, in order to provide each image pickup element with a process circuit.

However, in the above-described configuration (1), the light guide (entering/emerging) plane is inclined to the axis of the optical fiber, and the individual fiber plates are so arranged that the optical axes of the optical fibers mutually cross. It is difficult, with such configuration, to achieve compactization of the X-ray image pickup apparatus.

On the other hand, the above-described configuration (2) results in an increase in the dimension of the X-ray image pickup apparatus. Also as the alignment between each stepped portion and the image pickup element requires a high precision, the manufacturing process requires a large number of steps and also requires a highly precise aligning apparatus. In consideration of these facts, the configuration (2) is not practical.

Thus, the X-ray image pickup apparatuses of the conventional configurations have not been satisfactory in the increase in the size of the image pickup apparatus, in the cost reduction thereof and in the efficiency of the manufacturing process.

SUMMARY OF THE INVENTION

In consideration of the foregoing, an object of the present invention is to provide a large-area fiber plate suitable for compactization and cost reduction of the radiation image pickup apparatus and superior in the efficiency of the manufacturing process, and a radiation image pickup apparatus and a radiation image pickup system utilizing the same.

Another object of the present invention is to provide a method for producing a fiber plate and a radiation image pickup apparatus, capable of providing a large-area fiber plate, a radiation image pickup apparatus and a radiation image pickup system in inexpensive manner.

The present invention is featured in that, in a fiber plate in which plural individual fiber plates of a same thickness are so arranged in mutually adjacent manner as to provide a light guiding plane larger than that of an individual one fiber plate, each of the plural individual fiber plates is composed of a group of optical fibers having mutually parallel axes and the lateral faces of the plural individual fiber plates are so bonded that the axes of the optical fibers become mutually parallel.

In such invention, the axes of the optical fibers are preferably parallel or inclined to the normal line to the above-mentioned light guiding face. Also in such invention, at least either of the above-mentioned light guiding face or the above-mentioned lateral faces is preferably a polished surface.

Also in such invention, the above-mentioned lateral faces are preferably bonded by at least either of an adhesive or a metal.

Also in such invention, the portion of above-mentioned bonding is preferably a radiation intercepting bonded portion.

Also in such invention, the above-mentioned lateral faces preferably include a face crossing the normal line to the above-mentioned light guiding face.

The present invention is also featured in that, in a fiber plate in which plural individual fiber plates of a same thickness are so arranged in mutually adjacent manner as to provide a light guiding plane larger than that of an individual one fiber plate, each of the plural individual fiber plates is composed of a group of optical fibers having axes parallel to the normal line to the light guiding face, and the lateral faces of the plural individual fiber plates are so bonded that the axes of the optical fibers become mutually parallel, and the front face and the rear face constituting the light guiding faces of the fiber plate are same in area.

In such invention, the plural individual fiber plates are preferably bonded in the mutually parallel lateral faces thereof.

Also in such invention, the above-mentioned light guiding face is preferably a polished surface.

Also in such invention, the above-mentioned lateral face is preferably a polished face.

Also in such invention, the above-mentioned lateral faces are preferably bonded by at least either of an adhesive or a metal.

Also in such invention, the portion of above-mentioned bonding is preferably a radiation intercepting bonded portion.

Also in such invention, the above-mentioned lateral faces preferably include a face crossing the normal line to the above-mentioned light guiding face.

The present invention is further featured in that, in a radiation image pickup apparatus provided with a wavelength converting member for converting radiation into light, a photoelectric converting element for converting light into an electrical signal and a fiber plate positioned between the wavelength converting member and photoelectric converting element, the fiber plate are composed of plural individual fiber plates of a same thickness so arranged in mutually adjacent manner as to provide a light guiding plane larger than that of an individual one fiber plate, wherein each of the plural individual fiber plates is composed of a group of optical fibers having mutually parallel axes, and the lateral faces of the plural individual fiber plates are so bonded that the axes of the optical fibers become mutually parallel.

In such invention, the axes of the optical fibers are preferably parallel or inclined to the normal line to the above-mentioned light guiding face.

Also in such invention, at least either of the above-mentioned light guiding face or the above-mentioned lateral faces is preferably a polished surface.

Also in such invention, the above-mentioned lateral faces are preferably bonded by at least either of an adhesive or a metal.

Also in such invention, the portion of above-mentioned bonding is preferably a radiation intercepting bonded portion.

Also in such invention, the above-mentioned lateral faces preferably include a face crossing the normal line to the above-mentioned light guiding face.

Also in such invention, the width of the gap between the adjacent individual fiber plates is preferably smaller than the width of the pixel of the photoelectric converting element.

Also in such invention, it is preferable that the photoelectric converting element has plural pixels of mutually different light-receiving areas and that the width of the gap between the adjacent individual fiber plate is smaller than the width of a pixel having the smallest light-receiving area of the photoelectric converting element.

Also in such invention, the gap between the adjacent individual fiber plates is preferably positioned on the gap of chips constituting the photoelectric converting element.

Also in such invention, the gap between the adjacent individual fiber plates is preferably positioned on the effective pixel area of chips constituting the photoelectric converting element.

Also in such invention, the joint line formed by the gaps of the adjacent individual fiber plates crosses the joint line formed by the gaps of the chips constituting the photoelectric converting element with an angle larger than 0° and smaller than 90°.

The present invention is further featured in that, in a radiation image pickup apparatus provided with a wavelength converting member for converting radiation into light, a photoelectric converting element for converting light into an electrical signal and a fiber plate positioned between the wavelength converting member and photoelectric converting element, the fiber plate are composed of plural individual fiber plates of a same thickness so arranged in mutually adjacent manner as to provide a light guiding plane larger than that of an individual one fiber plate, wherein each of the plural individual fiber plates is composed of a group of optical fibers having axes parallel to the normal line to the above-mentioned light guiding plane;

the lateral faces of the plural individual fiber plates are so bonded that the axes of the optical fibers become mutually parallel, and the front surface and the rear surface constituting the light guiding planes of the fiber plate have a same area.

In such invention, the above-mentioned lateral faces are preferably polished faces.

Also in such invention, the above-mentioned light guiding faces are preferably polished faces.

Also in such invention, the above-mentioned lateral faces are mutually bonded by at least either of an adhesive or a metal.

Also in such invention, the portion of above-mentioned bonding is preferably a radiation intercepting bonded portion.

Also in such invention, the above-mentioned lateral faces preferably include a face crossing the normal line to the above-mentioned light guiding face.

Also in such invention, the width of the gap between the adjacent individual fiber plates is preferably smaller than the width of the pixel of the photoelectric converting element.

Also in such invention, it is preferable that the photoelectric converting element has plural pixels of mutually different light-receiving areas and that the width of the gap between the adjacent individual fiber plate is smaller than the width of a pixel having the smallest light-receiving area of the photoelectric converting element.

Also in such invention, the gap between the adjacent individual fiber plates is preferably positioned on the gap of chips constituting the photoelectric converting element.

Also in such invention, the gap between the adjacent individual fiber plates is preferably positioned on the effective pixel area of chips constituting the photoelectric converting element.

Also in such invention, the joint line formed by the gaps of the adjacent individual fiber plates crosses the joint line formed by the gaps of the chips constituting the photoelectric converting element with an angle larger than 0° and smaller than 90°.

The present invention is further featured in that, in a radiation image pickup apparatus consisting of an array of a plurality of radiation image pickup units, each provided with a wavelength converting member for converting radiation into light, a photoelectric converting element chip for converting light into an electrical signal and a fiber plate positioned between the wavelength converting member and photoelectric converting element, the lateral faces of the plural individual fiber plates of the plural radiation image pickup units are so bonded that the axes of the optical fibers become mutually parallel.

In such invention, the above-mentioned lateral faces are preferably polished surfaces.

Also in such invention, the above-mentioned light guiding face is preferably a polished face.

Also in such invention, in the above-mentioned radiation image pickup unit, the wavelength converting member, the photoelectric converting element chip and the individual fiber plate have a substantially same size.

The present invention is further featured by a method for producing a fiber plate, comprising:

a step of preparing plural individual fiber plates of a same thickness, each consisting of a group of optical fibers having mutually parallel axes;

a step of arranging the plural individual fiber plates in such adjacent manner as to provide a light guiding face larger in area than the light guiding face of each individual one fiber plate; and a step of so bonding the lateral faces of the plural individual fiber plates that the axes of the optical fibers become mutually parallel.

In such invention, the method preferably comprises:

a step of bonding at least two of the plural individual fiber plates thereby forming a set of individual fiber plates; and a step of further bonding plural sets of the individual fiber plates thereby forming the above-mentioned fiber plate.

Also in such invention, it is preferable to polish lateral faces of the set of the individual fiber plates and then to bond the plural sets of the individual fiber plates in such a manner that the lateral faces are mutually adjacent.

Also in such invention, the lateral faces of the adjacent individual fiber plates are bonded with a metal or an adhesive.

Also in such invention, the surfaces of the plural individual fiber plates are preferably polished after the fiber plates are bonded.

Also in such invention, the method preferably comprises:

a step of preparing plural individual fiber plates of a same thickness, each consisting of a group of optical fibers having axes parallel to the normal line to the light guiding face;

a step of arranging the plural individual fiber plates in such adjacent manner as to provide a light guiding face larger in area than the light guiding face of each individual one fiber plate; and a step of so bonding the lateral faces of the plural individual fiber plates that the axes of the optical fibers become mutually parallel.

Also in such invention, the method preferably comprises:

a step of bonding at least two of the plural individual fiber plates thereby forming a set of individual fiber plates; and a step of further bonding plural sets of the individual fiber plates thereby forming the above-mentioned fiber plate.

Also in such invention, it is preferable to polish lateral faces of the set of the individual fiber plates and then to bond the plural sets of the individual fiber plates in such a manner that the lateral faces are mutually adjacent.

Also in such invention, the lateral faces of the adjacent individual fiber plates are bonded with a metal or an adhesive.

Also in such invention, the surfaces of the plural individual fiber plates are preferably polished after the fiber plates are bonded.

Also in such invention, the method preferably comprises:

a step of preparing plural individual fiber plates each consisting of a group of optical fibers having mutually parallel axes;

a step of arranging the plural individual fiber plates in such adjacent manner as to provide a light guiding face larger in area than the light guiding face of each individual one fiber plate; and a step of bonding the lateral faces of the plural individual fiber plates and then polishing the surfaces of the fiber plates.

The present invention is further featured by a method for producing a radiation image pickup apparatus comprising:

a step of preparing the above-described fiber plate; and a step of bonding to the photoelectric converting element.

In such invention, it is preferable, after the bonding of the fiber plate with planarized surfaces and the photoelectric converting element, to bond the sheet-shaped wavelength converting member to the fiber plate.

Also in such invention, it is preferable, after the bonding of the fiber plate with planarized surfaces and the sheet-shaped wavelength converting member, to bond the photoelectric converting element thereto.

The present invention is further featured by a radiation image pickup system comprising:

signal processing means for processing a signal from the above-mentioned radiation image pickup apparatus;

recording means for recording the signal from the signal processing means;

display means for displaying the signal from the signal processing means; and a radiation source for generating the radiation.

BRIEF DESCRIPTION OF THE DRAWINGS

FIGS. 31A, 31B, 31C and 31D are schematic views showing a method producing a radiation image pickup apparatus in an embodiment of the present invention;

FIGS. 32A, 32B, 32C, 32D and 32E are schematic views showing a method producing a radiation image pickup apparatus in another embodiment of the present invention;

DETAILED DESCRIPTION OF THE PREFERRED EMBODIMENTS

Now the present invention will be clarified in detail with reference to the accompanying drawings.

Figure 1:
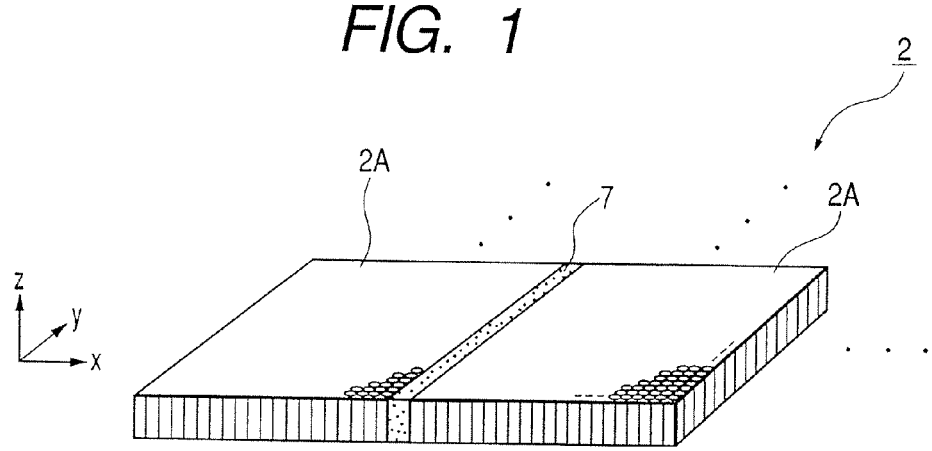
FIG. 1 is a schematic perspective view of a fiber plate of the present invention.

FIG. 1 is a schematic perspective view showing the basic configuration of a fiber plate of the present invention;

A single (individual or discrete) fiber plate 2 is composed of plural optical fibers, and a bonding material 7 bonds at least two adjacent individual fiber plates.

The individual fiber plate to be employed in the present invention can be obtained, for example, by forming an integral parallel bundle of 1,000 to 10 million optical fibers of a diameter of 1 to 100 μm and cutting such bundle into a plate of a thickness of 1 to 20 mm in such manner that a plane perpendicular to the axes of the optical fiber is exposed. Therefore, taking the light guiding plane (light entering and emerging faces) of the individual fiber plate at x-y plane, the axes of all the optical fibers are approximately parallel to the z-axis and are parallel to the normal line to the light entrance/exit faces within a tolerance of about ±1°, thus forming an angle of 0°±1°.

Plural individual fiber plates of a same thickness are arranged along the x-y plane in such a manner that the light entrance/exit plane becomes coplanar and the lateral faces of the individual fiber plates are so bonded that the axes of the optical fibers become mutually parallel, whereby the fiber plates constitute a large-area fiber plate providing a large-area light entrance/exit plane. The thicknesses of these fiber plates need not be exactly same but can have a certain tolerance.

In another form, the large-area fiber plate can also be produced by preparing plural individual fiber plates of a parallelogram cross-section having axis of the optical fibers inclined to the x-y plane and bonding the lateral faces of such fiber plates in such a manner that the axes become mutually parallel.

Though only two individual fiber plates are illustrated, the number thereof is not particularly limited. Also the thickness of the individual fiber plates need not be exactly equal but can have a certain tolerance. It is also preferable, if necessary, to polish the surface of the fiber plate 2 after the mutual bonding of the individual fiber plates 2A.

The optical fiber can be composed of a known material such as glass, and preferably of a light transmitting material such as lead-containing glass, containing a radiation intercepting material such as lead.

The bonding material can be composed of an organic or inorganic bonding material as will be explained later. Particularly preferred is a material equal or close, in the characteristics such as thermal expansion coefficient, to the fiber plate.

The size of the individual fiber plate is not particularly limited and can be, for example, several tens to several thousands square centimeters.

Figure 2:
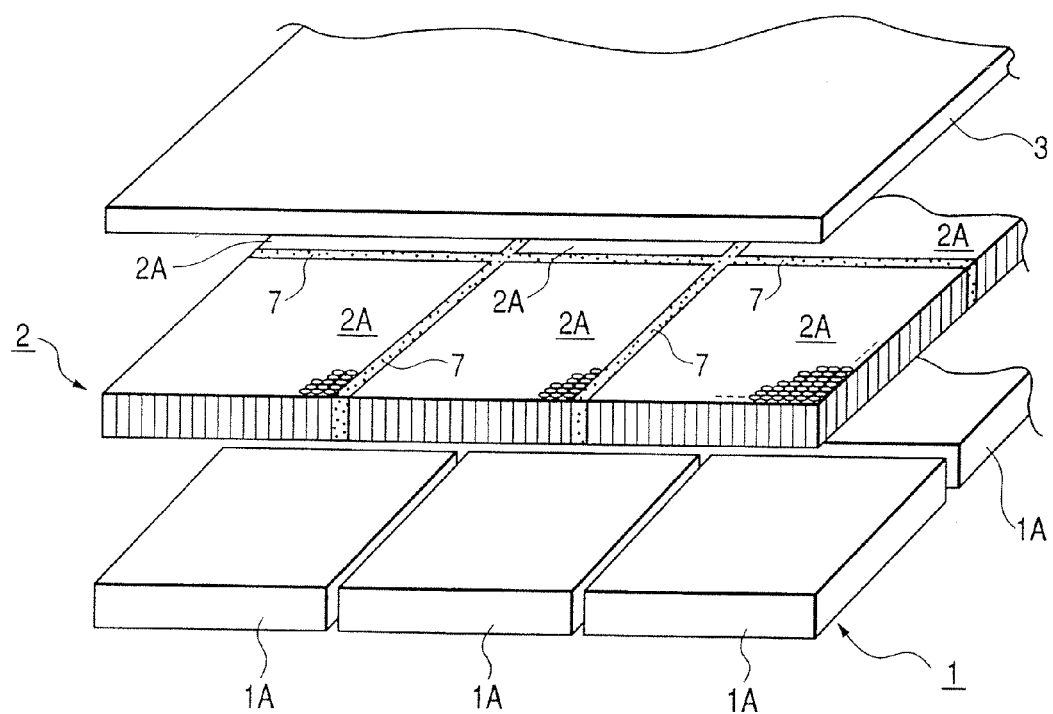
FIG. 2 is a schematic view showing the configuration of a radiation image pickup apparatus of the present invention.

FIG. 2 is a schematic-view showing the basic configuration of a radiation image pickup apparatus employing the above-described fiber plate.

An image pickup element 1A is composed of an integrated circuit chip such as a CCD image sensor chip, a CMOS image sensor chip, a bipolar image sensor chip, a CMD image sensor chip or a thin film transistor image sensor chip, and plural image pickup elements are arranged to constitute a large-area image pickup element (photoelectric converting element) 1.

Also plural individual fiber plates 2A are arranged to constitute a large-area fiber plate 2.

A wavelength converting member 3 is a layer-structured member called a scintillator or a phosphor, composed of a gadrinium sulfur oxide such as $Gd_2O_2S(Tb)$ or an alkali-metal halide represented by cesium iodide such as $CsI(Tl)$.

It is preferred that the light guiding area of the bonded large-area fiber plate 2 is made equal to or larger than the effective light-receiving area of the bonded large-area image pickup element 1 and that the area of the wavelength converting member 3 is made equal to or larger than the light guiding area of the bonded large-area fiber plate 2.

When a radiation enters the upper surface of the wavelength converting member 3 from above, the wavelength converting member 3 emits light of visible wavelength range. The fiber plate 2 positioned between the wavelength converting member 3 and the image pickup element 1 guides the light to the light-receiving area thereof. The light entering the light-receiving area is subjected to photoelectric conversion in each pixel and is read as an electrical signal.

The fiber plate 2A, if composed of a radiation intercepting fiber plate, can intercept entry of the radiation into the image pickup element 1, thereby suppressing errors and noise generation in the image pickup element.

In FIG. 2, the number of the individual fiber plates 2A is illustrated same as that of the image pickup element chips 1A, but, in the present invention, they need not be mutually same and can be different. Preferably the individual fiber plates 2A are made larger in dimension and smaller in number than the image pickup element chips 1A.

The image pickup apparatus of the present invention can be advantageously employed in an X-ray image pickup apparatus to be explained in the following, but such application is not restrictive and it can also be applied to a radiation image pickup apparatus for detecting image a radiation other than X-ray, such as α-ray, β-ray or γ-ray.

Embodiment 1

Figure 3:
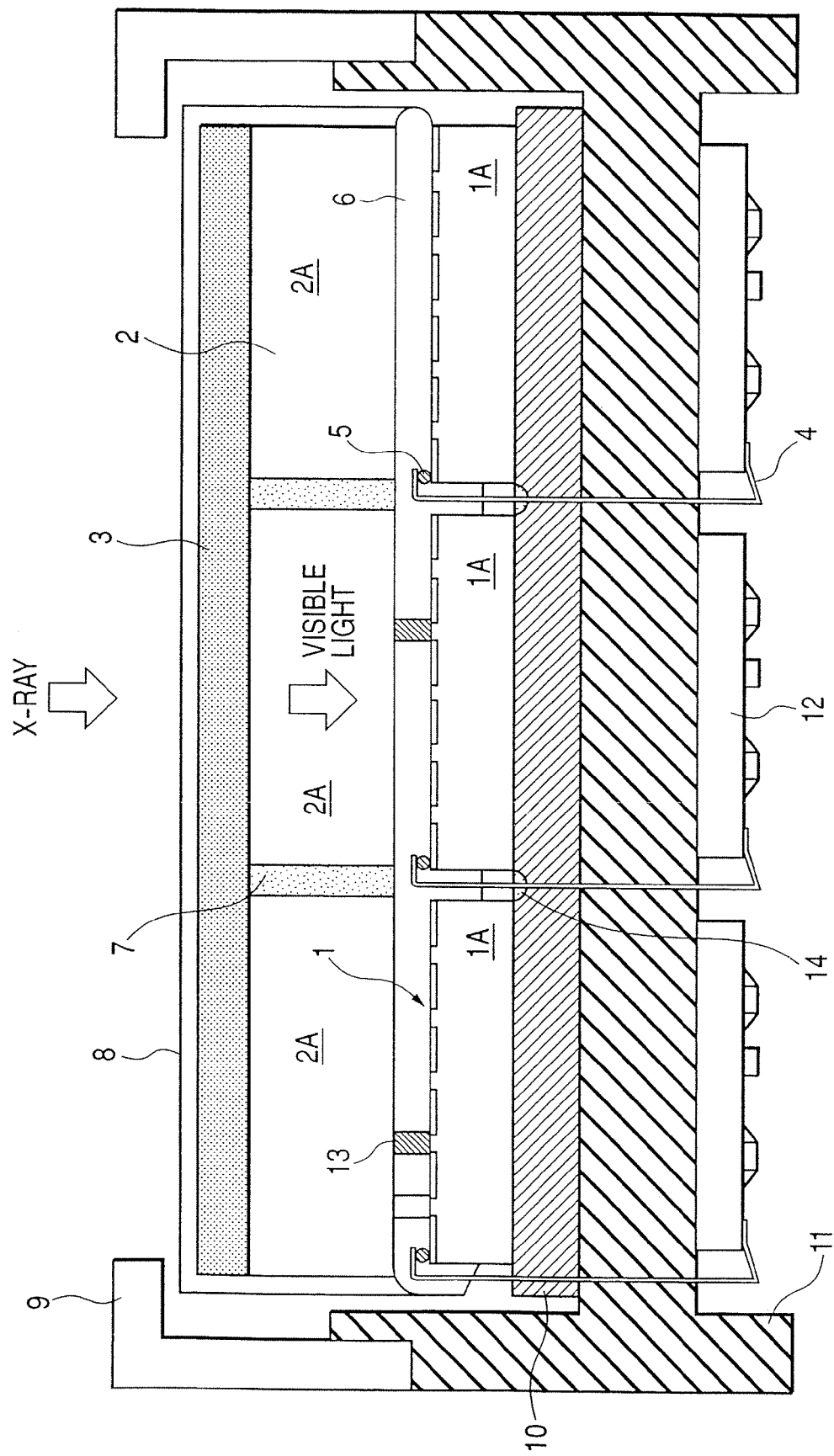
FIG. 3 is a schematic cross-sectional view of an X-ray image pickup apparatus constituting an embodiment of the present invention.

FIG. 3 is a cross-sectional view of an X-ray image pickup apparatus constituting an embodiment 1 of the present invention. FIG. 3 shows an apparatus provided with a phosphor (wavelength converting member) 3 serving as a scintillator for converting X-ray into light of a wavelength detectable by an image pickup element (photoelectric converting element) such as visible light, an individual fiber plate 2A composed of plural optical fibers for guiding the light, converted by the wavelength converting member 3, to an image pickup element, and an image pickup element 1 provided with a photoelectric converting photosensor for converting the light into an electrical signal.

The apparatus is further provided with an adhesive 7 for mutually bonding the individual fiber plate 2A, and, if necessary, with an elastic transparent adhesive 6 for adhering a large-area fiber plate 2 with an image pickup element 1 including plural pixels, a flexible board 4 having wirings for outputting the electrical signal from each image pickup element chip 1A to the exterior, a bump 5 for electrically connecting the flexible board 4 and the image pickup element chip 1A, a printed circuit board 12 to which the flexible board 4 is connected, an aluminum protective sheet 8 for protecting the phosphor 3, a base substrate 10 for mounting the image pickup element 1, a base casing 11 for holding the base substrate 10, a casing cover 9 provided in the base casing 11, a spacer 13 provided between the image pickup element 1 and the fiber plate 2 for maintaining a constant gap therebetween, and a filler adhesive 14 for maintaining the transparent adhesive 6 between the fiber plate 2 and the image pickup element 1.

The X-ray image pickup apparatus shown in FIG. 3 is prepared by adhering the image pickup element 1 and the large-area fiber plate 2 provided with the plural individual fiber plates 2A, by means of the transparent adhesive 6.

Figure 4:
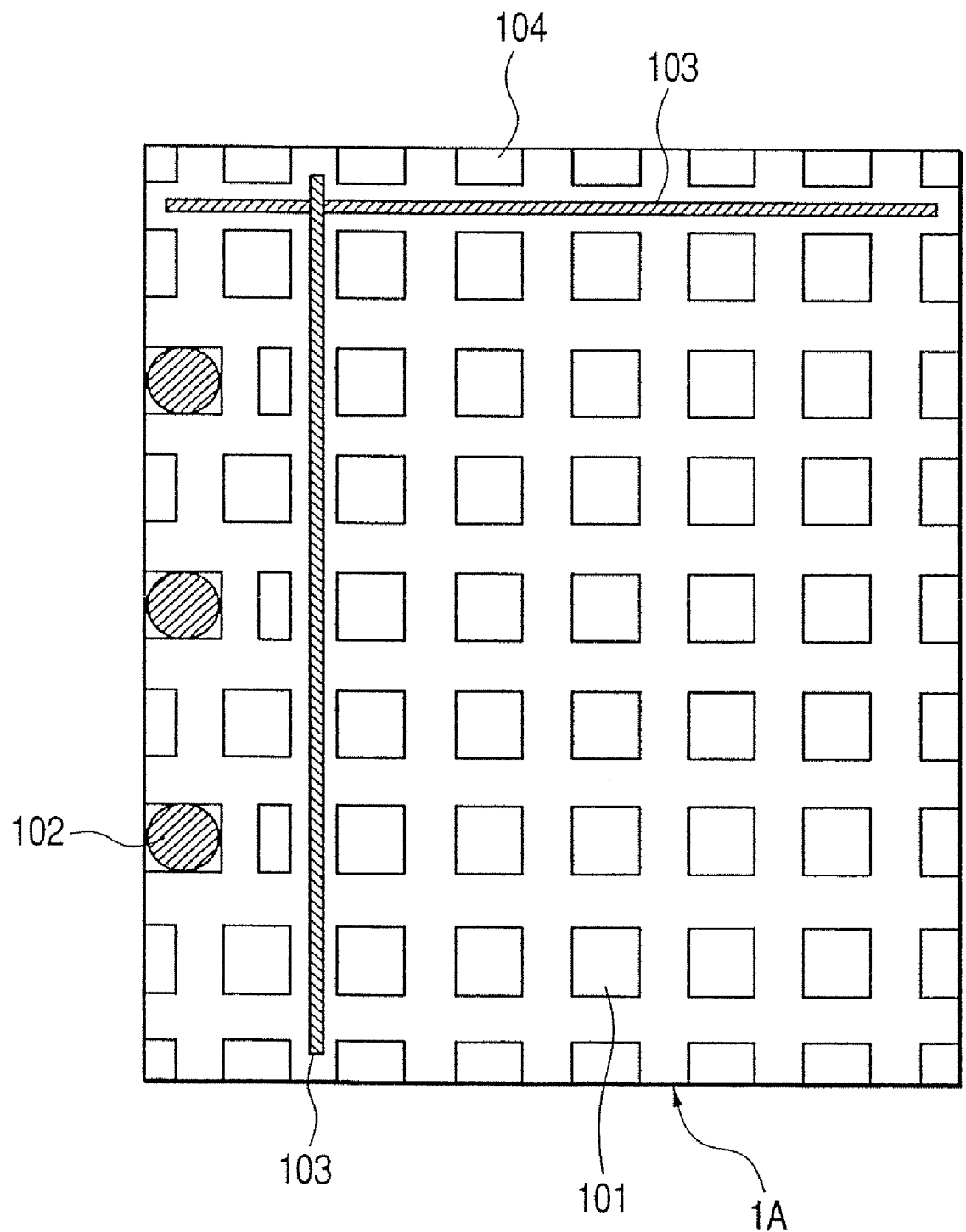
FIG. 4 is a schematic plan view of image pickup elements to be employed in the present invention.

FIG. 4 is a plan view showing an example of the schematic configuration of the image pickup element employable in the present invention.

FIG. 4 shows an ordinary pixel 101 having two-dimensionally arranged plural photosensors, plural peripheral pixels 1204 provided outside a driving circuit 103, a driving circuit 103 for driving the peripheral pixels 104 in succession, and input/output terminals 102 of the image pickup element 1A.

The ordinary pixels 101 are arranged on the approximately entire area of the image pickup element chip 1A, with a pitch for example of 160 µm as will be explained later. Between the ordinary pixels 101, the drive circuit 103 is dividedly positioned. As the peripheral pixel 104 is smaller in area than the ordinary pixel 101, the pixel signal is compensated to cancel the difference in the area.

Figure 5A:
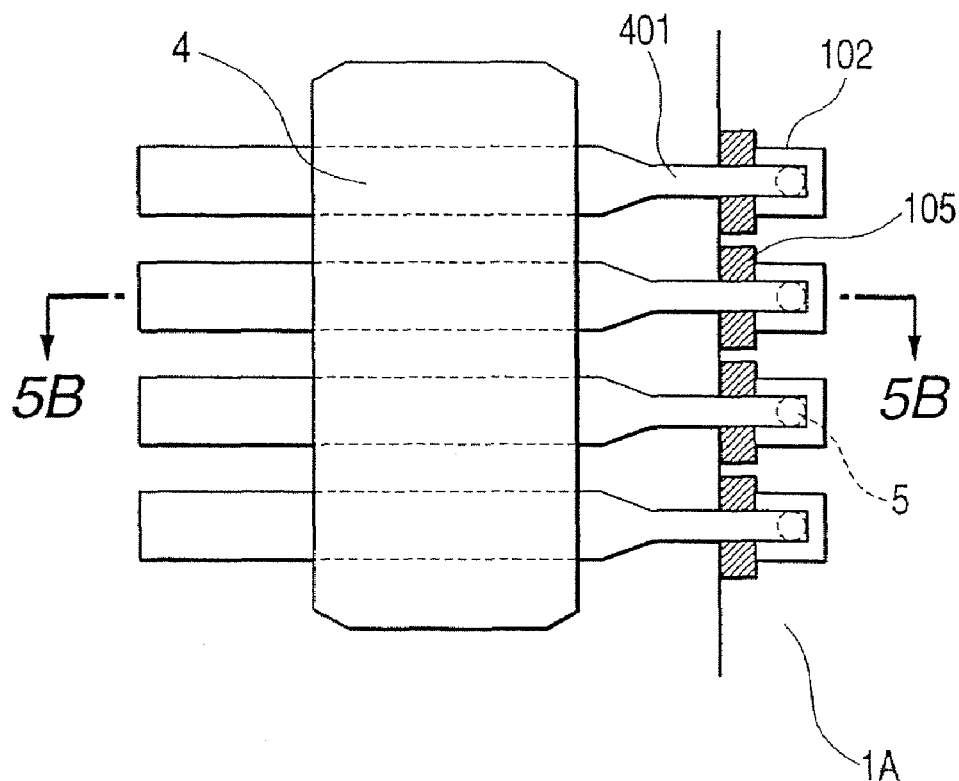
FIGS. 5A and 5B are schematic views showing the configuration in the vicinity of external connection terminals of the image pickup elements.
Figure 5B:
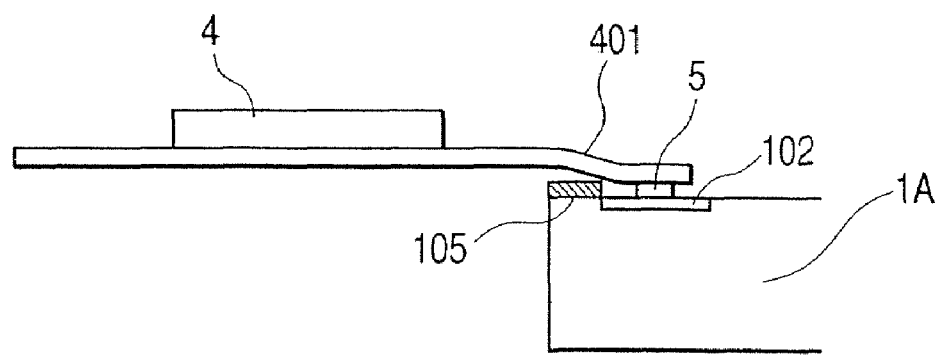

FIGS. 5A and 5B show the configuration in the vicinity of the output terminals of the image pickup element employed in the present invention. FIG. 5A is a plan view in the vicinity of a bump 5 of the image pickup element chip 1A and the flexible wiring board 4, and FIG. 5B is a cross-sectional view along a line 5B in FIG. 5A.

There are shown a connecting bump 5, an inner lead 401 of the flexible wiring board 4 to be connected to the bump 5, and an organic insulating layer 105 composed for example of a polyimide resin layer, for preventing the shortcircuiting between the end of the image pickup element chip 1A and the inner lead 401 and the end chipping of the image pickup element 1.

Figure 6:
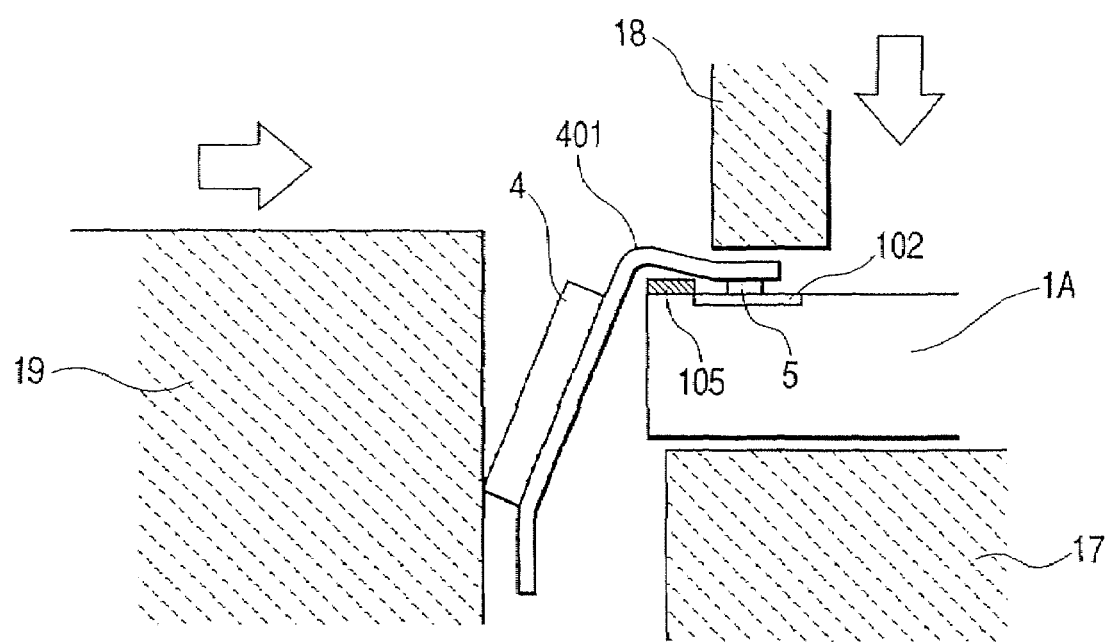
FIG. 6 is a schematic view showing the configuration in the vicinity of external connection terminals of the image pickup elements.

FIG. 6 is a schematic view showing a method of electrical connection between the bump 5 and the flexible circuit board 4 shown in FIGS. 5A and 5B.

At first, for example a polyimide resin layer is formed as the organic insulating layer 105, with a thickness of 25 µm, at an end of the image pickup element chip 1A.

Then for forming electrical connection between the bump 5 and the flexible wiring board 4, a bump 5 is formed for example by a stud bump process or by plating on an input/output terminal 102 of the image pickup element chip 1A.

Then the bump 5 and the inner lead 401 are fused for example by ultrasonic bonding, whereby the metal constituting the bump 5 and the metal constituting the inner lead 401 are electrically and physically connected by metal-metal bonding. As an example, the inner lead 401 can be formed by etching a copper foil, and plating with nickel and gold to a thickness of about 18 µm, and the total thickness of the flexible wiring board can be about 50 µm.

Then, while the image pickup element chip 1A is vertically sandwiched between supports 17 and 18, a jig or tool 19 is moved with respect thereto in a direction indicated by an arrow, whereby the inner lead 401 is bent downwards by about 90° at the end of the image pickup element 1A.

Figure 7A:
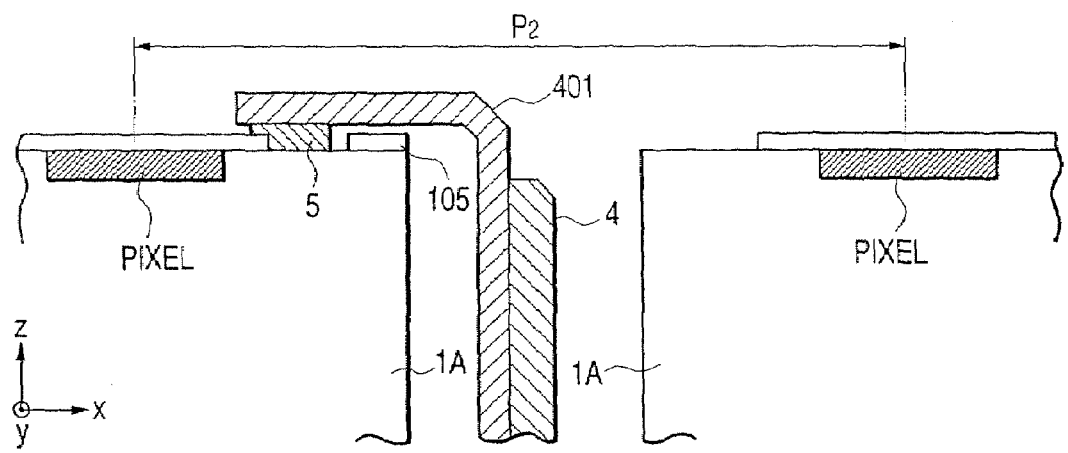
FIGS. 7A and 7B are schematic views showing the configuration between adjacent image pickup elements.
Figure 7B:
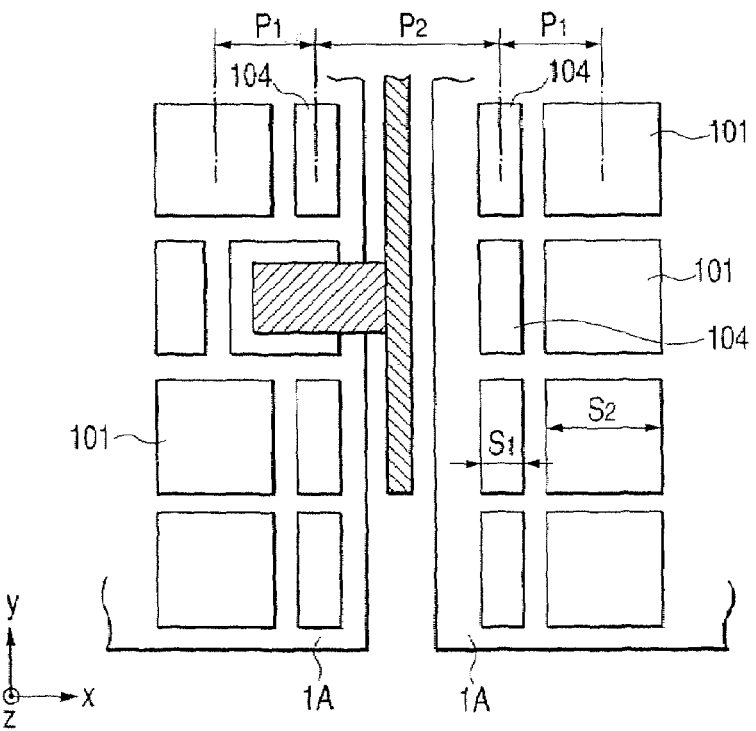

FIGS. 7A and 7B are respectively a cross-sectional view and a plan view of the vicinity of the flexible wiring board of the image pickup element employed in the present invention.

As shown in FIGS. 7A and 7B, in the X-direction, the width S1 of the peripheral pixel 104 is smaller than the width S2 of the ordinary pixel 101 (S1<S2).

In FIG. 7B, the pitch P2 of the peripheral pixels 104 is shown different from the pitch P1 between the ordinary pixel 101 and the peripheral pixel 104, but these pitches are preferably same (P2=P1) and also equal to the picth P between the ordinary pixels (P1=P2=P).

In this manner the pixel pitch becomes same in all the peripheral pixels and the ordinary pixels, thereby improving the image quality.

FIGS. 8A to 8F show the bonding process between the image pickup element and the base substrate employed in the present invention. At first plural image pickup element chips 1A provided with the flexible board 4 are placed on a stage 32, utilizing an alignment camera 33 and an alignment head 31 movable in the X, Y, Z and θ (rotational) directions.

Figure 8A:
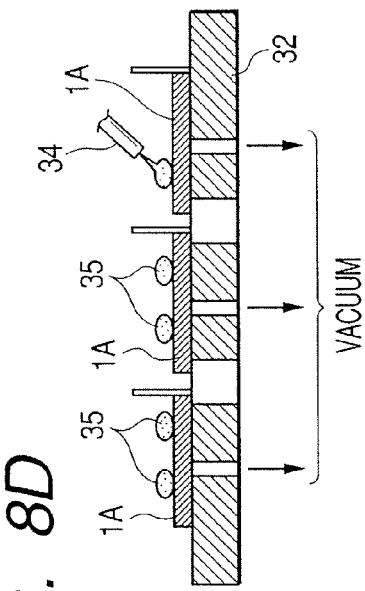
FIGS. 8A, 8B, 8C, 8D, 8E and 8F are schematic views showing a method for producing an image pickup apparatus.

In this state, each image pickup element chip 1A is fixed on the stage 32 by suction, by an unrepresented vacuum apparatus, through a hole 32A formed on the stage 32 (FIG. 8A).

In this state, each image pickup element chip 1A is inspected for the required function. More specifically, an inspection jig 34 is used to inspect whether the image pickup element chip 1A has been damaged for example by electrostatic charge (FIG. 8).

Figure 8D:
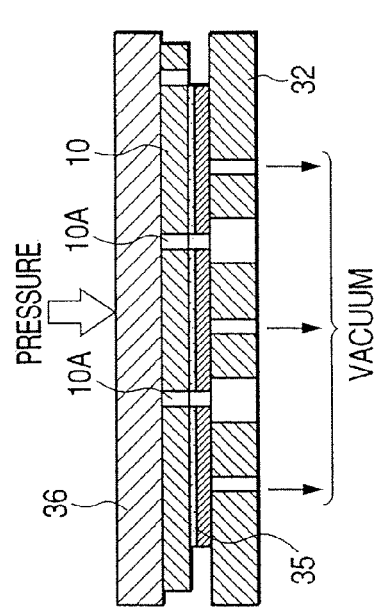
Figure 8B:
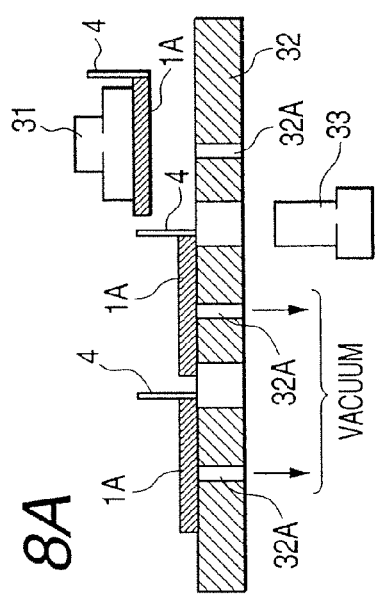
Figure 8E:
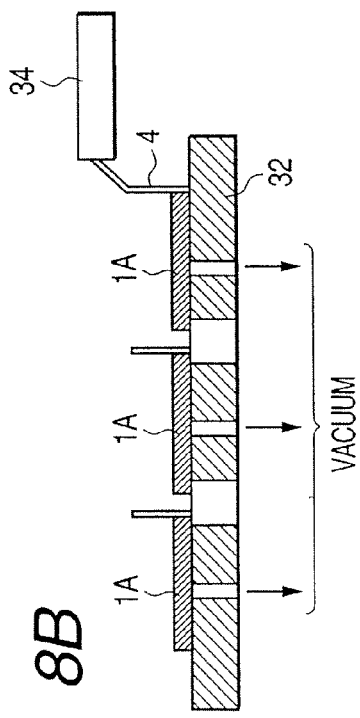
Figure 8C:
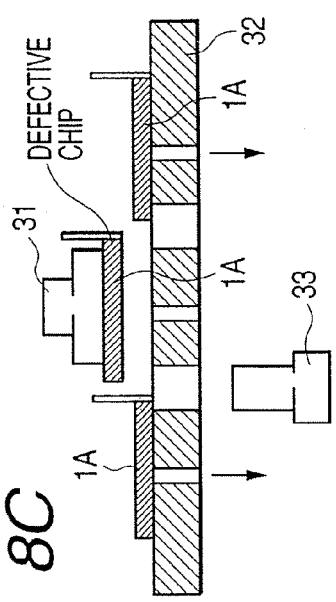

If a defect is found in the image pickup element chip 1A in the inspection, the vacuum apparatus below such chip is turned off and the defective chip is replaced by the alignment head 31 (FIG. 8C).

Then adhesive 35 such as UV curable resin or silicone resin is coated by an adhesive dispenser 34 onto the upper face of the image pickup element chip 1A (FIG. 8D).

Then the flexible wiring board 4 is inserted into an elongated hole 10A provided in the base substrate 10, which is then brought into contact with the image pickup element 1 and the adhesive is set for fixation by UV irradiation or by pressurizing (FIG. 6E).

It is advantageous to match the size of the individual fiber plate 2A with that of the image pickup element chip 1A and to mutually align the two. Also the base substrate 10 is preferably composed of glass or permalloy (iron+nickel) in consideration of matching with the image pickup element 1 in thermal expansion coefficient etc.

Figure 8F:
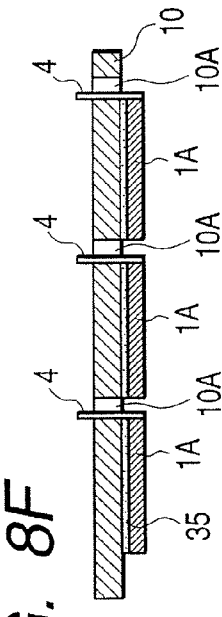

After the fixation by bonding of the image pickup element 1 and the base substrate 10, the vacuum apparatus is turned off and the image pickup element 1 and the base substrate 10 are removed from the jig 36 such as the stage (FIG. 8F).

In this manner there can be obtained the large-area image pickup element 1 by bonding plural image pickup element chips 1A.

Figure 9A:
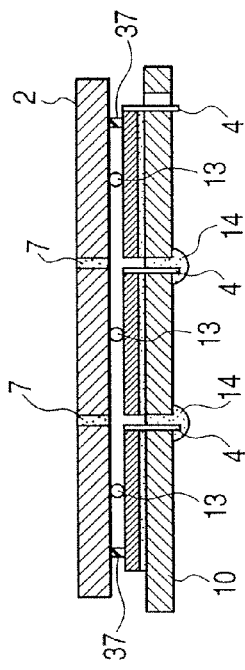
FIGS. 9A, 9B, 9C and 9D are schematic views showing a method for producing an image pickup apparatus of the present invention.
Figure 9B:
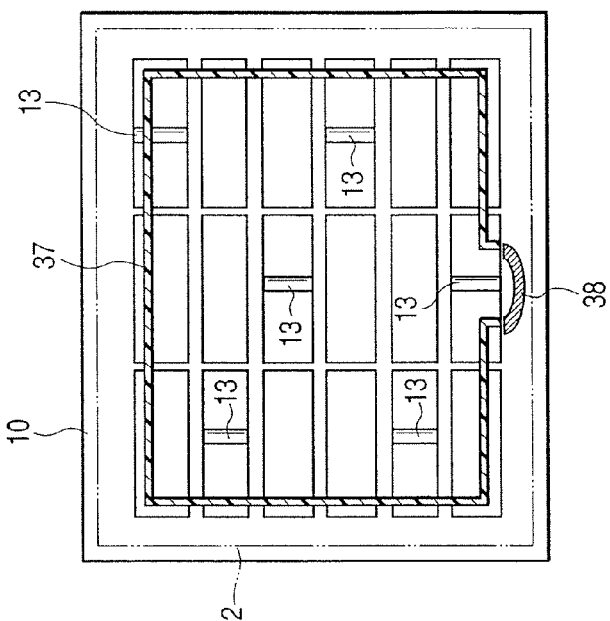
Figure 9C:
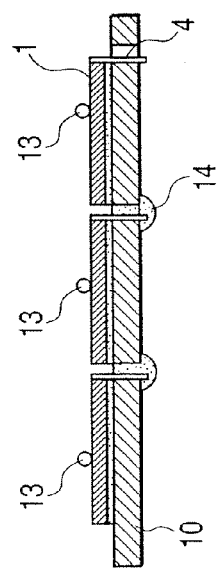
Figure 9D:
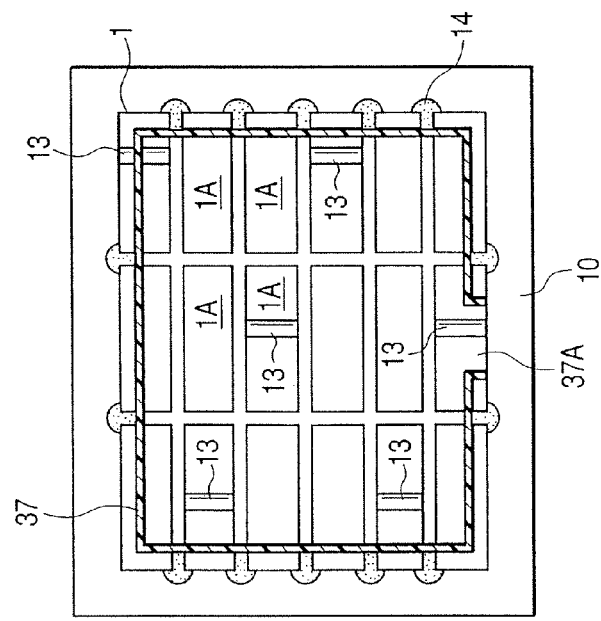

FIGS. 9A to 9D are schematic views showing steps of adhering the large-area image pickup element employed in the present invention and the aforementioned large-area fiber plate, wherein FIGS. 9A and 9C are cross-sectional views and FIGS. 9B and 9D are plan views.

On each image pickup element chip 1A adhered to the base substrate 10, a spacer 13 is positioned in order to maintain the gap to the large-area fiber plate 2 (FIG. 9A).

The spacer 13 can be spherical or cylindrical. Then sealing material 37 is coated on the image pickup element 1 and filler adhesive 14 is coated so as to fill the gap of the image pickup elements 1 (FIG. 9B).

The sealing material 37 is provided in a part thereof with an aperture 37A through which transparent adhesive 6 is filled by vacuum injection as will be explained later. In order to prevent leakage of vacuum in such injection, the filler adhesive 14 is filled also in the gaps between the image pickup element chips 1A on the upper surface of the base substrate 10.

Then the large-area fiber plate 3 is adhered onto the large-area image pickup element 1, across the spacer 13 (FIG. 9C). Also if necessary, there is preferred a configuration in which the adhesive 7, used for mutual bonding of the fiber plates 2, is positioned directly above the gap between the image pickup element chips 1A or between the pixels.

Then pressing or pressing under heating is executed to maintain a uniform gap between the image pickup element chip 1A and the fiber plate and to set the sealing material 37. Then, in a vacuum chamber, the gap between the large-area fiber plate 2 and the image pickup element 1 is maintained under a reduced pressure, and a port (not shown) containing the transparent adhesive 6 is attached to the aperture 37A, and the pressure is returned to the atmospheric pressure whereby the transparent adhesive is filled into the gap between the fiber plate 2 and the image pickup element 1.

Then the aperture 37A is sealed with a sealant 38 (FIG. 9D).

Then the sheet-shaped wavelength converting member 3 is adhered onto the fiber plate 2 thereby completing the X-ray image pickup apparatus.

The wavelength converting member 3 may also be formed by evaporating the material thereof or coating a mixture of powdered phosphor and a binder on the fiber plate 2, and, in such case, the wavelength converting member 3 is provided on the fiber plate 2 prior to the step shown in FIG. 9C.

Now reference is made again to FIG. 3 for explaining the function of the X-ray image pickup apparatus. An unrepresented X-ray source is provided at the side of the wavelength converting member 3 and X-ray is irradiated from the X-ray source in a state where an object is positioned between the X-ray source and the X-ray image pickup apparatus. The X-ray irradiates the object, and is transmitted with the Roentgen information having a difference in the intensity, generated in transmitting the object, to the X-ray image pick up apparatus.

In the X-ray image pickup apparatus, the wavelength converting member 3 converts the X-ray into light such as visible light, corresponding to the intensity of the X-ray. The light obtained by such conversion is transmitted through the fiber plate 2 to the image pickup element 1. Since the fiber plate 2 and the image pickup element 1 are mutually adhered by the transparent adhesive 6, the light enters the image pickup element 1 without attenuation in passing the transparent adhesive 6.

The light also enters the adhesive 7 and is absorbed or refleccted therein, thereby lowering the light transmittance. Such light will generate a line defect if it enters the pixel of the image pickup element 1, but, by selecting the individual fiber plate 2A and the image pickup element chip 1A of a same size and mutually aligning the two, there can be obtained a configuration in which the light from the adhesive 7 does not affect much the pixel of the image pickup element 1.

The image pickup element chip 1A converts the entering light into an electrical signal corresponding to the light intensity. Such electrical signal is read out, through the bump 6, to the lead 401 of the flexible wiring board 4, in response to an instruction of an unrepresented readout circuit. The electrical signal read out to the flexible wiring board 4 is supplied to an external circuit formed on a printed circuit board 12 for A/D conversion followed by image processing.

Producing Method for Large-area Fiber Plate

In the following there will be explained a method for producing the large-area fiber plate to be employed in the present invention.

FIGS. 10A to 10D are schematic views showing an example of the producing method for the large-area fiber plate employed in the present invention.

Figure 10A:
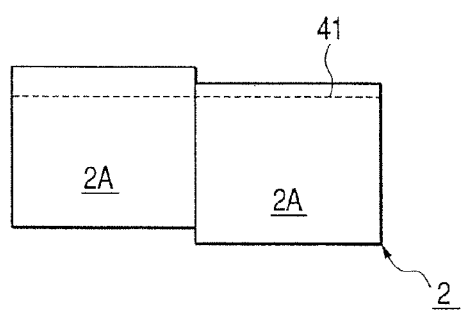
FIGS. 10A, 10B, 10C and 10D are schematic views showing a method for producing a fiber plate of the present invention.

At first, two individual fiber plates 2A are mutually bonded by adhesive, as shown in FIG. 10A. In such operation, the individual fiber plates are often bonded with a slight mutual displacement as shown in FIG. 10A, even if the bonding is executed carefully. If all the individual fiber plates 2A are bonded in this manner, there will result an unnecessarily large gap. In this producing method, in order to avoid such unnecessarily large gap, at least a lateral face of the fiber plates 2 bonded with mutual displacement is polished to a broken-lined portion 41 to obtain an aligned flat lateral face 2B as shown in FIG. 10B.

Figure 10B:
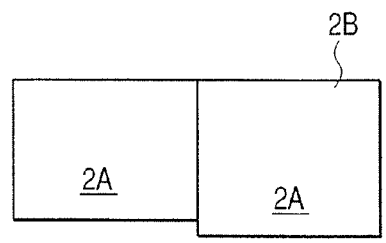
Figure 10C:
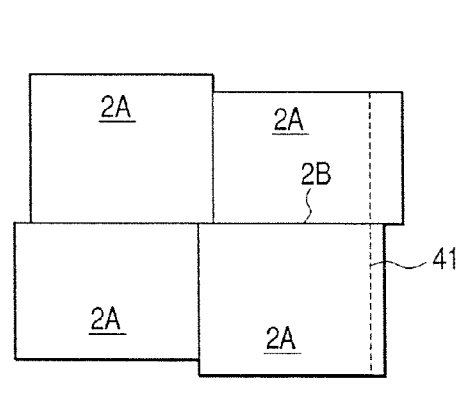

Then another set of the two individual fiber plates 2A is prepared by a procedure similar to that shown in FIGS. 10A and 10B, and such two sets of the fiber plates are bonded in such a manner that the respective flat polished lateral faces 2B mutually abut (FIG. 10C).

Figure 10D:
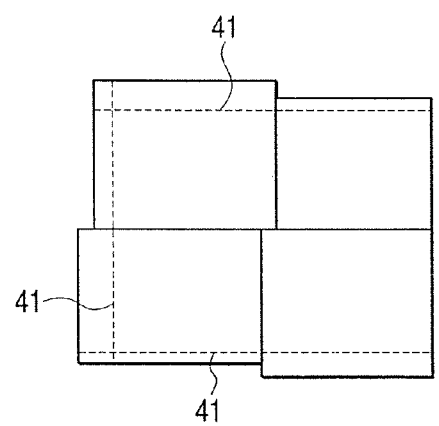

Then, if necessary one of the remaining four lateral faces is polished to a broken line 41. Also the remaining three lateral faces may be polished as shown in FIG. 10D to reduce the gap between the adjacent lateral faces there obtaining a large-area fiber plate of which all the four lateral faces are flat.

In the foregoing there has been explained an example of bonding four individual fiber plates 2A to obtain a large-area fiber plate 2, but, in practice, there are bonded a predetermined number of the individual fiber plates 2A in order to obtain the fiber plate 2 of a desired size.

Figure 11A:
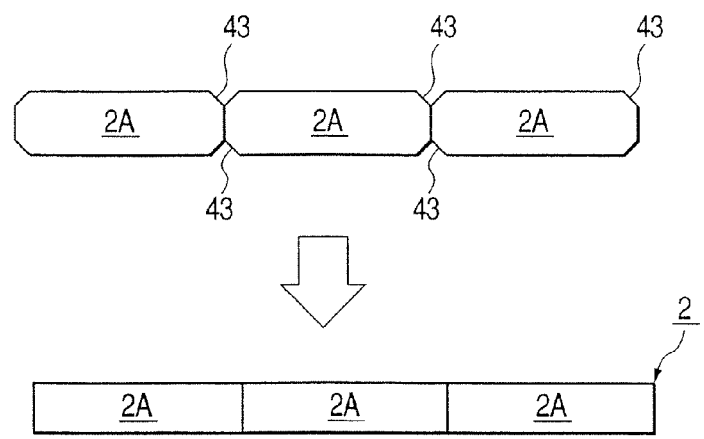
FIGS. 11A and 11B are schematic views showing another example of the method for producing the fiber plate of the present invention.
Figure 11B:
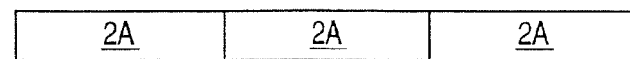

FIGS. 11A and 11B are schematic cross-sectional views showing another producing method for the fiber plate to be employed in the present invention. Now there will be explained an example of producing the large-area fiber plate 2 by bonding six fiber plates 2A, but FIGS. 11A and 11B show only three individual fiber plates 2A therein. In practice, there are bonded the fiber plates 2A of a predetermined number in order to obtain the large-area fiber plate 2 of a desired size.

In the cross section of the large-area fiber plate 2 obtained by the method shown in FIGS. 10A to 10D, a chipped portion 43 as shown in FIG. 11A is generated at the corner in the polishing operation of the lateral face or in the handling in different steps. Therefore, the front and rear surfaces constituting the light guiding faces of the large-area fiber plate after bonding are polished until such chipped portion 43 is removed, thereby providing the large-area fiber plate 2 without the chipped portion as shown in FIG. 11B.

The large-area fiber plate 2 thus obtained and shown in FIG. 11B is adhered to the large-area image pickup element 1 across the spacer 13 if necessary.

Embodiment 2

Figure 12:
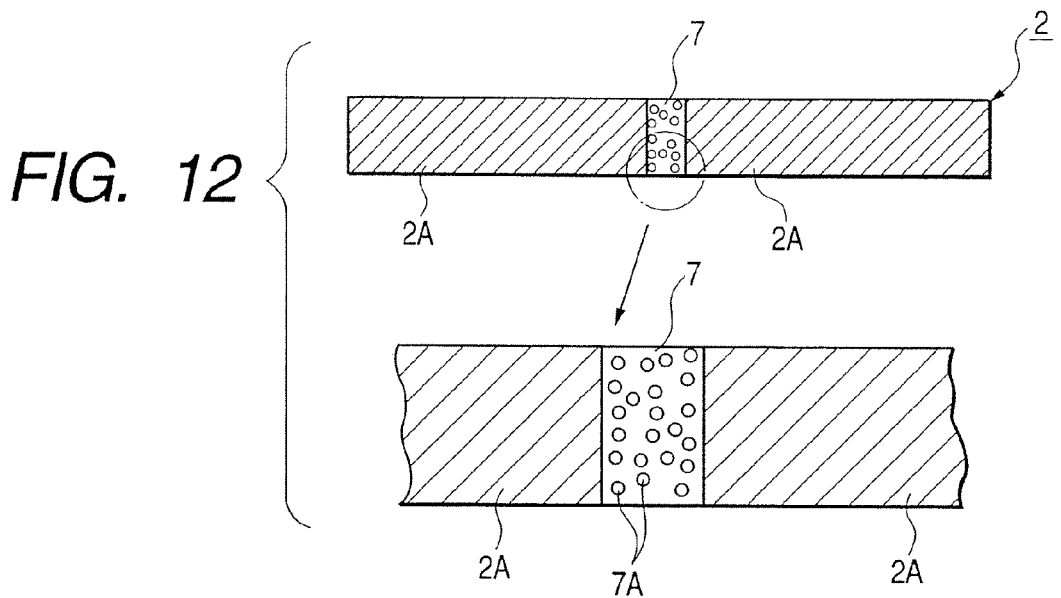
FIG. 12 is a schematic view showing the configuration of the fiber plate constituting an embodiment of the present invention.

FIG. 12 is a cross-sectional view of a large-area fiber plate 2 of an embodiment 2 of the present invention.

The large-area fiber plate 2 shown in FIG. 12 is featured by employing, as the adhesive 7, an adhesive material composed of for example epoxy resin and containing an X-ray interrupting member 7A such as lead.

Examples of the adhesive include ethylene-vinyl acetate copolymer, carboxyl-denatured ethylene-vinyl acetate copolymer, ethylene-isobutylacrylate copolymer, polyamide, polyester, polymethyl methacrylate, polyvinylether, polyvinylbutyral, polyurethane, styrene-butylene-styrene (SBS) copolymer, carboxyl-denatured SBS copolymer, styrene-isoprene-styrene (SIS) copolymer, styrene-ethylene-butylene-styrene (SEBS) copolymer, maleic acid-denatured SEBS copolymer, polybutadiene rubber, chloroprene rubber (CR), carboxyl-denatured CR, styrene-butadiene rubber, isobutylene-isoprene copolymer, acrylonitrile-butadiene rubber (NBR), carboxyl-denatured NBR, epoxy resin, silicone rubber (SR) and mixtures thereof.

Also if necessary there may be added, as an auxiliary reactant or a crosslinking agent, phenolic resin, polyols, isocyanates, melamine resin, urea resin, urotropine resin, amines, acid anhydrides, peroxides, metal oxides, organic acid metal salts such as chromium trifluoroacetate, alkoxides of titanium, zirconia, aluminum etc., organometallic compounds such as dibutyl tin dioxide, photoinitiators such as 2,2-diethoxyacetophenone or benzyl, sensitizers such as amines, phosphor compounds, chlorine compounds etc., a hardening agent, a vulcanizing agent, a controlling agent, an antideterioration agent, a heat resistance improving agent, a thermal conduction improving agent, a softening agent, a coloring agent, various coupling agents, or a metal deactivating agent.

As the intercepting member 7A, there is employed at least a metal selected from iron, cobalt, nickel, copper, zinc, silver, tin, gadrinium, tungsten, platinum, gold, lead and bismuth, or an alloy containing such metal or a compound of such metal. Such metal, alloy of compound may be used in combination with lead-containing solder paste such as Pb—Sn, lead-free solder paste or silver paste. Otherwise such metal, alloy or compound may be used in a particular form, and, in such case, there may also be employed an inorganic or organic particle (carbon particle or plastic ball) with a coating formed by plating or sputtering.

The large-area fiber plate of the present embodiment can prevent unhindered transmission of the radiation through the joint portion of the individual fiber plates, since such joint portion is composed of the radiation intercepting adhesive.

The X-ray image pickup apparatus utilizing such large-area fiber plate can prevent entry of the X-ray, entering the wavelength converting member 3 and not converted into the light therein, into the image pickup element 1. More specifically, the X-ray, entering the wavelength converting member 3 and not converted into the light, is intercepted by the material itself, containing lead or the like, of the large-area fiber plate 2 and/or the intercepting adhesive 7. It is thus made possible to suppress the noise generation caused by the X-ray entry into the image pickup element 1.

Figure 13A:
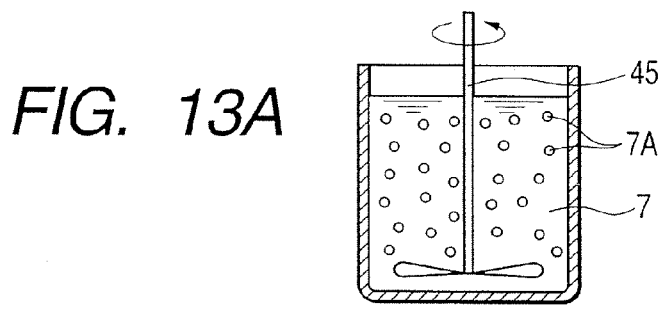
FIGS. 13A, 13B and 13C are schematic views showing a method for producing the fiber plate shown in FIG. 12.
Figure 13B:
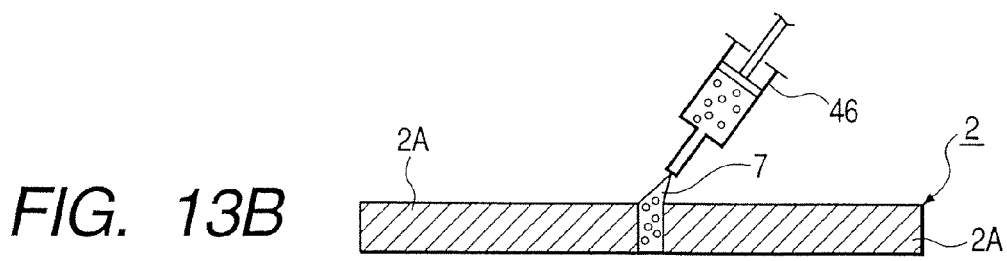
Figure 13C:
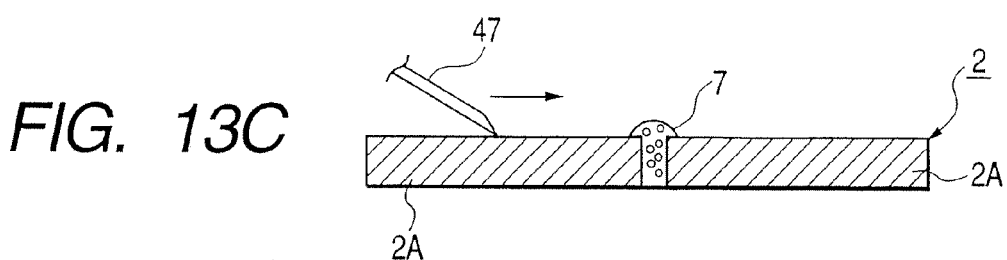

FIGS. 13A to 13C are schematic views showing a producing method for the large-area fiber plate shown in FIG. 12.

At firsts as shown in FIG. 13A, the adhesive and the X-ray intercepting member 7A are agitated for example with a stirring rod. After the foams generated by agitation are removed, the bonding material consisting of the adhesive containing the X-ray intercepting member 7A is filled into the gap between the fiber plates by a dispenser 46 or by screen printing (FIG. 13B). The filling operation is preferably executed under a reduced pressure in order to facilitate escaping of the air in the gap.

Then the adhesive is set under mutual pressurizing of the individual fiber plates 2A. The setting can be achieved by UV irradiation or by heating within a range from the room temperature to 200° C. Thereafter the adhesive overflowing on the upper surface of the fiber plate 2 is scraped off (FIG. 13C). In this manner there can be obtained a large-area fiber plate 2.

Embodiment 3

Figure 14:
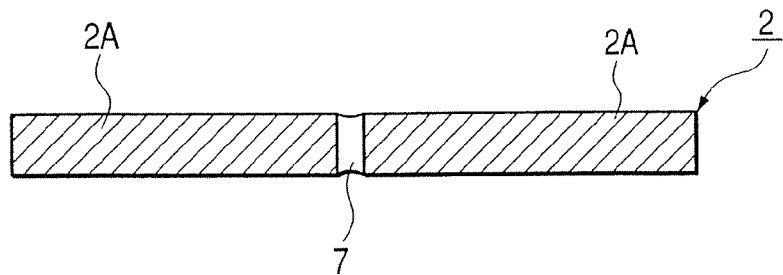
FIG. 14 is a schematic cross-sectional view of a fiber plate of another embodiment of the present invention.

FIG. 14 is a schematic cross-sectional view of a large-area fiber plate of an embodiment 3 of the present invention. In this embodiment, the large-area fiber plate 2 is prepared by bonding the individual fiber plates 2A with a low melting metal (having a melting point not exceeding 330° C.) and liquid flux.

The low melting metal to be employed in the present invention can be an alloy containing at least two of the metals such as Pb, Sn, Bi, Sb, In, Ag, Cd etc. for example cocrystalline solder such as Sn—Pb (63:37 wt. %) or high melting solder such as Sn—Pb (10:90 wt. %). Also the low melting metal is desirably in particular form for easy mixing with the liquid flux.

Also as the liquid flux, there can be employed a liquid flux containing a resin component such as purified rosin, hydrogenated rosin or polymerized rosin and a solvent component for example an alcohol such as terpineol, 1,4-butanediol or methyl cellosolve or a ketone such as methylethylketone, methylisoproopylketone or methylisobutylketone as the essential components, and further suitably containing other additives for example a viscosity regulating agent such as polyethylene glycol, polyvinyl butyral or petroleum resin and an active agent such as maronic acid, succinic acid or triethanolamine.

Also there can be employed an aqueous liquid flux containing a polyhydric alcohol component such as polyethylene glycol, glycerin or polyvinyl alcohol and water which is a solvent component, as the essential components, and further suitably containing additives for example a viscosity regulating agent such as polyacrylamide, and an active agent such as an organic acid, an organic or inorganic halide, diethylamine hydrochloric acid salt. Particularly preferred is aqueous liquid flux.

Figure 15A:
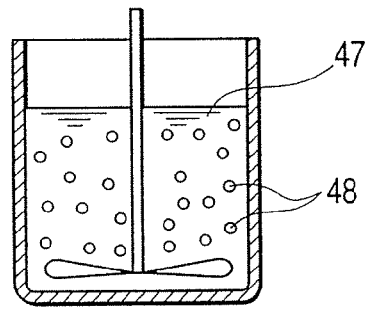
FIGS. 15A, 15B and 15C are schematic views showing a method for producing the fiber plate shown in FIG. 14.
Figure 15B:
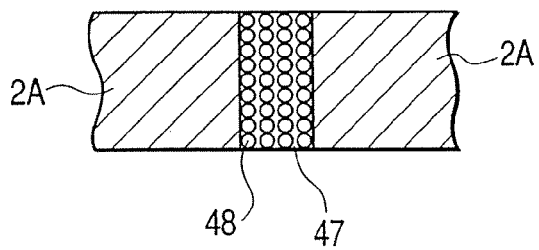
Figure 15C:
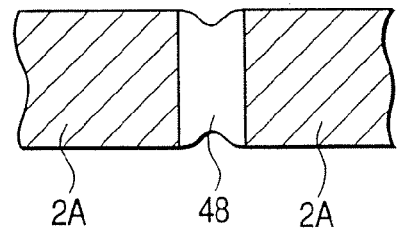

FIGS. 15A to 15C are schematic views showing a producing method for the large-area fiber plate shown in FIG. 14.

At first, as shown in FIG. 15A, the powdered low melting metal 48 and the liquid flux 47 are mixed. After the foams generated by agitation are removed, the liquid flux 47 containing the X-ray intercepting low melting metal 48 is filled into the gap between the fiber plates by a dispenser or by screen printing (FIG. 15B). The filling operation is preferably executed under a reduced pressure in order to facilitate escaping of the air in the gap.

Then the individual fiber plates 2A are mutually pressed and the low melting metal 48 is fused at the same time by heating at a temperature exceeding the melting point. Thereafter the low melting metal 48 eventually overflowing on the upper surface of the fiber plate 2 is scraped off. In this manner there can be obtained a large-area fiber plate 2 (FIG. 15C).

Embodiment 4

Figure 16:
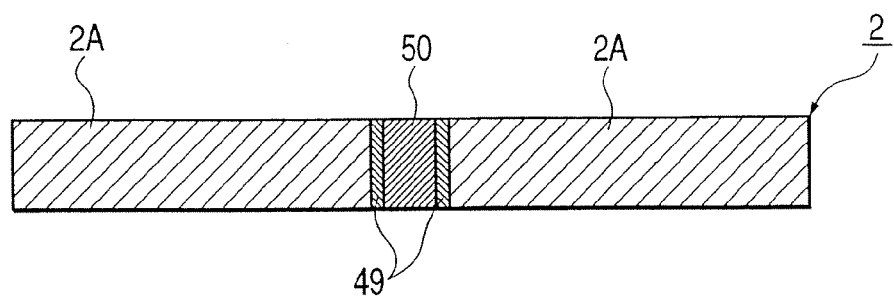
FIG. 16 is a schematic cross-sectional view of a fiber plate of still another embodiment of the present invention.

FIG. 16 is a schematic cross-sectional view of a large-area fiber plate of an embodiment 4 of the present invention. In this embodiment, the large-area fiber plate 2 is prepared by bonding the individual fiber plates 2A with a first metal layer 49 and a second metal layer 50.

Figure 17A:
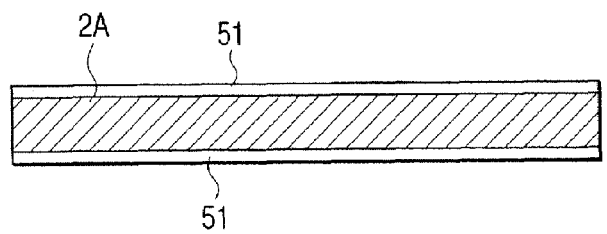
FIGS. 17A, 17B, 17C, 17D and 17E are schematic views showing a method for producing the fiber plate shown in FIG. 16.
Figure 17B:
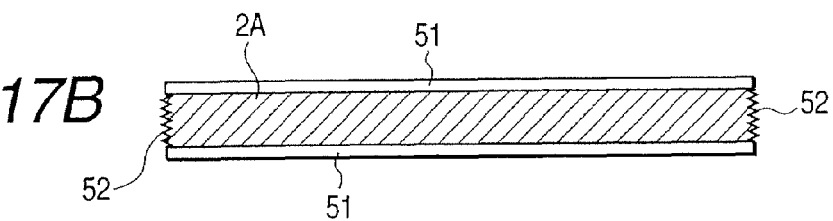
Figure 17C:
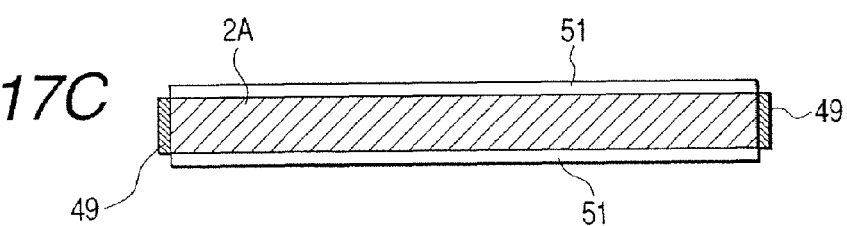

FIGS. 17A to 17C are schematic views showing a producing method for the large-area fiber plate shown in FIG. 16.

At first both surfaces of the individual fiber plate 2A are coated with acid etching resist 51 such as a photosensitive film resist (FIG. 17A).

Then the resist 51 is closely adhered, by heating, to the fiber plate 2A. Then, in order to improve adhesion of the glass with the first metal layer 49 to be explained later, the end face of the fiber plate 2 is etched with fluoric acid, potassium fluoride or acidic ammonium fluoride to form a coarse surface 52 (FIG. 17B).

Then, on the etched end face (coarse surface 52), a first metal layer 49 for example of nickel or copper is formed by electroless plating (FIG. 17C).

Figure 17D:
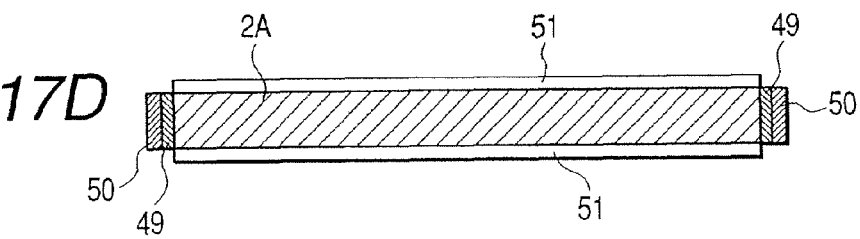

Then, on the first metal layer 49, a second metal layer 50 composed of an alloy of low melting metals is formed by electroplating (FIG. 17D). It is difficult to plate the second metal layer 50 on an insulating material such as glass. For this reason the above-mentioned first metal layer 49 is provided at first to form a conductive substrate and the second metal layer 50 is then formed by electroplating.

Figure 17E:
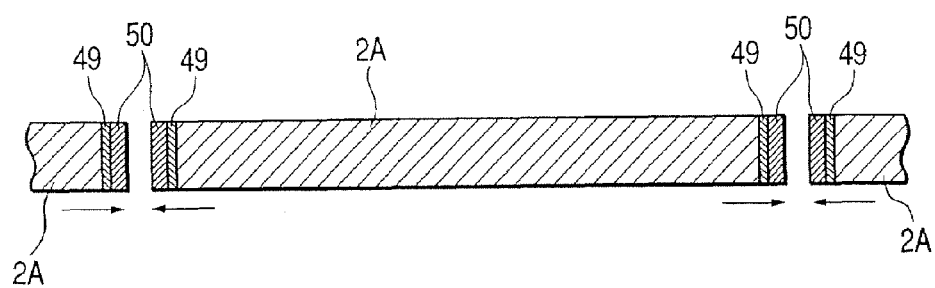

Then, after the resist 51 is peeled off, the individual fiber plates 2A are mutually pressed and the second metal layer 50 is heated at a temperature exceeding the melting point but not exceeding 330° C. (FIG. 17E).

Thereafter the first and second metal layers 49, 50 eventually overflowing on the upper surface of the fiber plate 2 is scraped off. In this manner there can be obtained a large-area fiber plate.

In the second to fourth embodiments, as explained in the foregoing, the fiber plates 2A are mutually connected with the bonding material 7 with X-ray intercepting property. Thus, by employing the large-area fiber plate of these embodiments in the radiation image pickup apparatus as shown in FIGS. 2 and 3, the X-ray not converted into light by the wavelength converting member 3 and emitted toward the fiber plate is intercepted by the base member of the fiber plate. In this manner the image pickup element 1 can be shielded from X-ray and there can be suppressed the noise generation.

Embodiment 5

Figure 18:
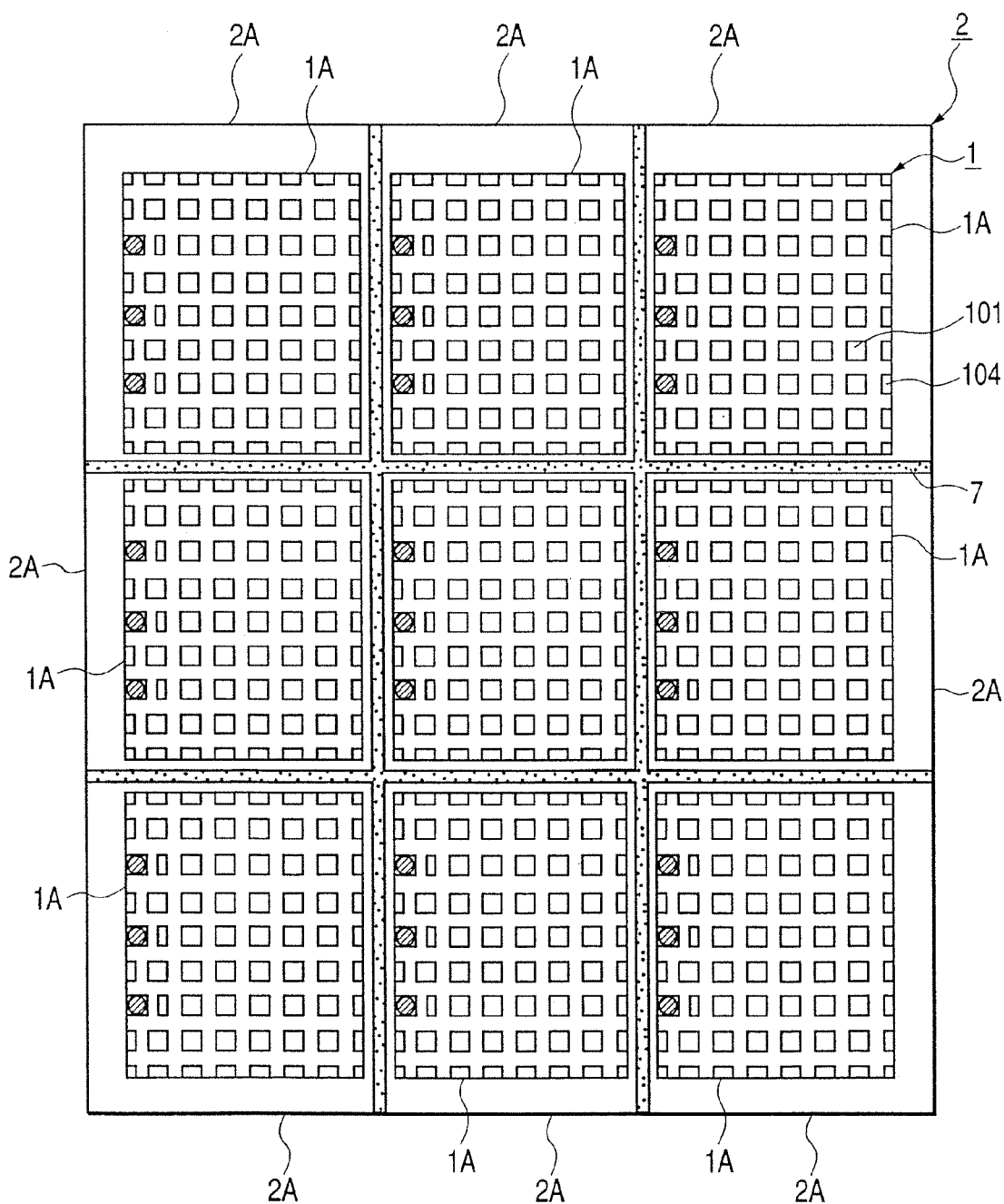
FIG. 18 is a schematic plan view of an X-ray image pickup apparatus constituting another embodiment of the present invention.
Figure 19:
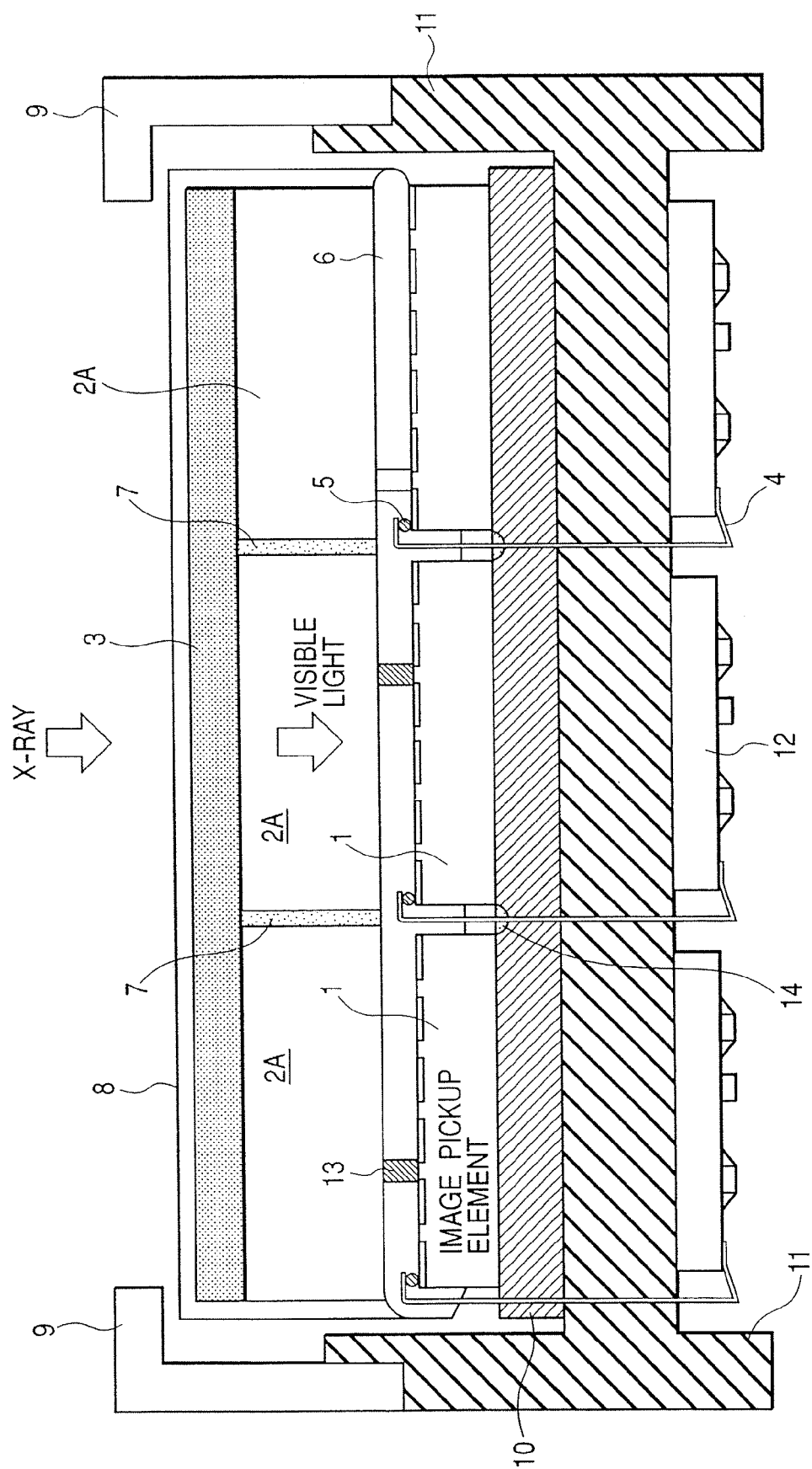
FIG. 19 is a schematic cross-sectional view of the X-ray image pickup apparatus shown in FIG. 18.

FIGS. 18 and 19 are respectively a plan view and a cross-sectional view of an embodiment of the X-ray image pickup apparatus of the present invention.

The basic configuration is same as that of the image pickup apparatus shown in FIGS. 2 and 3, except that the large-area fiber plate 2 and the large-area image pickup element 1 are adhered with mutual alignment in such a manner that a joint line formed by the bonding portions 7 of the individual fiber plates 2A is positioned above the gaps of the image pickup element chips 1A. More specifically, the width of the joint line consisting of the bonding portions 7 is made smaller than the gap between the image pickup element chips 1A so that the joint line does not cover the pixel areas even in the presence of a slight positional displacement.

The bonding material employed in the bonding portion 7 is preferably composed of a material equal to or same as the fiber plate in the characteristics such as thermal expansion coefficient. In the present embodiment, the bonding material can be transparent or opaque since the joint of the fiber plates is aligned with that of the image pickup elements.

Embodiment 6

Figure 20:
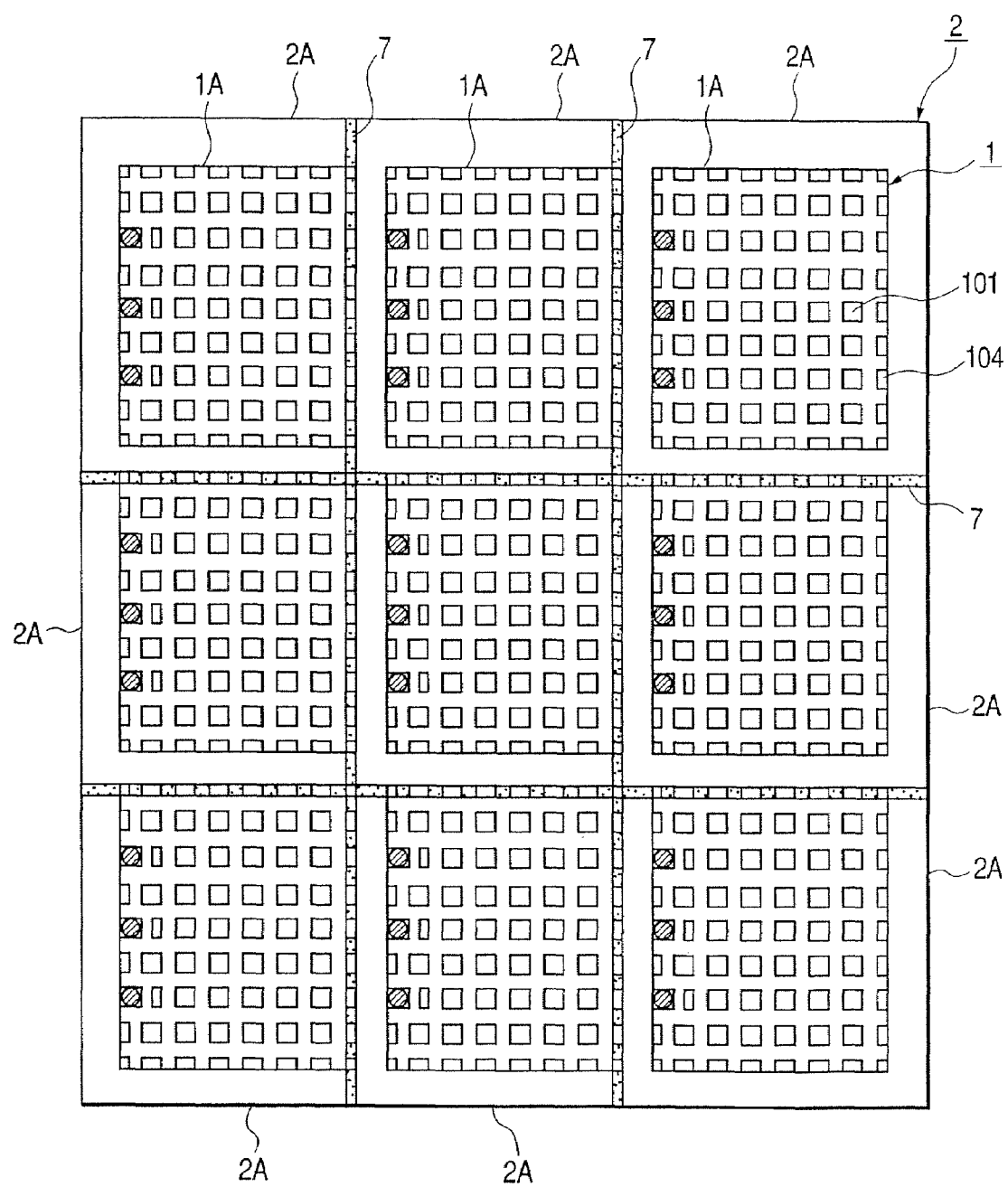
FIG. 20 is a schematic plan view of an X-ray image pickup apparatus constituting still another embodiment of the present invention.
Figure 21:
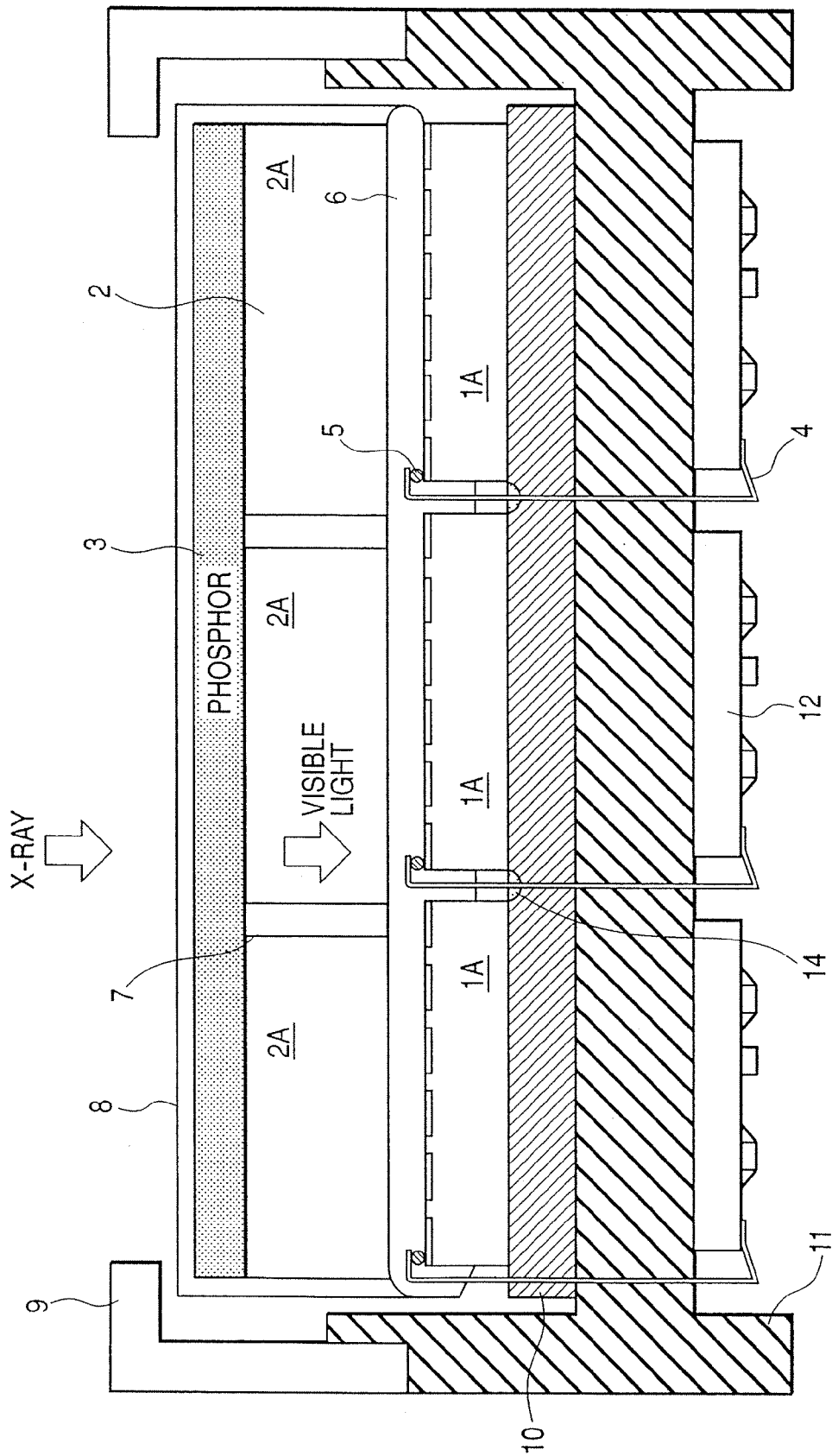
FIG. 21 is a schematic cross-sectional view of the X-ray image pickup apparatus shown in FIG. 20.

FIGS. 20 and 21 are respectively a plan view and a cross-sectional view showing another embodiment of the X-ray image pickup apparatus.

In case, as shown in FIGS. 20 and 21, the joint portion 7 of the fiber plates is so positioned, with a positional displacement, as to cover the peripheral pixels 104 of the image pickup element 1, the difference in the optical transmittance between the joint portion 7 and the fiber plate 2A results in a line defect or a pixel defect because the pixel of the row positioned under such joint portion 7, particularly the peripheral pixel 104, is smaller in size. A loss in sensitivity is unavoidable even in the larger ordinary pixel 101. Also the leaking X-ray, not converted into light but transmitted by the phosphor may enter the image pickup element through the joint portion 7, thereby generating a line-shaped shot noise with a deterioration in image quality, and leading to deterioration of the element.

In the X-ray image pickup apparatus shown in FIGS. 18 and 19, the joint of the fiber plates is aligned with that of the image pickup elements. Such configuration prevents the light, entering from the phosphor through the joint of the fiber plate, from entering the pixel row of the image pickup elements, thereby avoiding the line defect. Also the leaking X-ray from the phosphor is prevented from entering the image pickup elements through the joint of the fiber plate, thereby avoiding line-shaped shot noise.

However, in case the number of the individual fiber plates is different from that of the image pickup element chips, there is encountered a situation where the joint of the individual fiber plates cannot be matched with that of the image pickup element chips.

The following embodiment discloses a radiation image pickup apparatus capable of avoiding line defect even in such case.

Embodiment 7

Figure 22:
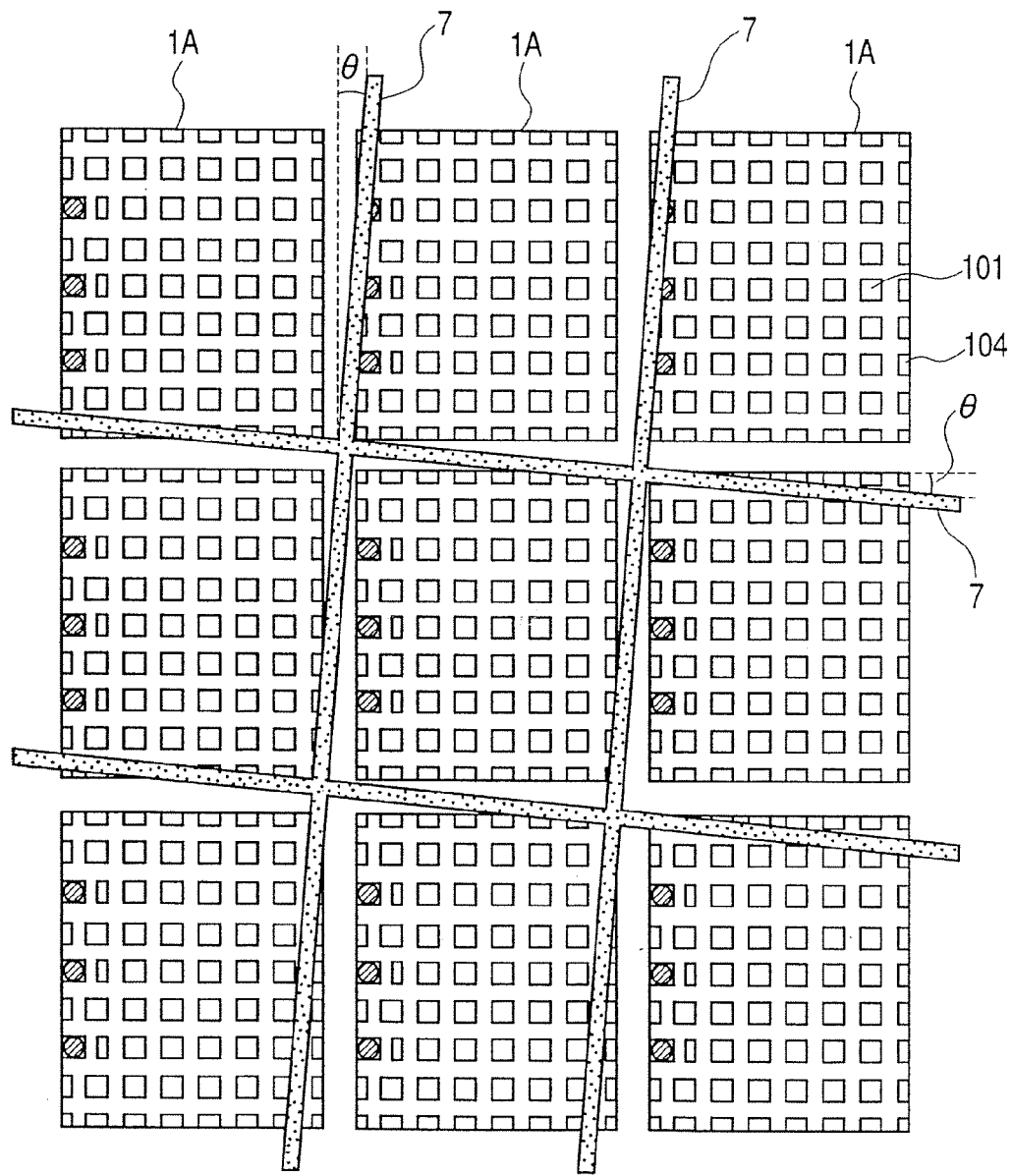
FIG. 22 is a schematic plan view of an X-ray image pickup apparatus constituting another embodiment of the present invention.

In the X-ray image pickup apparatus shown in FIG. 22, the joint line consisting of the bonding portions 7 of the individual fiber plates and the line of the pixel row of the image pickup elements are mutually inclined (angle θ≠0). Such configuration allows to prevent the entry of the light entering through the bonding portions of the fiber plates into all the pixels on a pixel row, thereby preventing the generation of the line defect. Even if the light from the bonding portions 7 of the fiber plates enters a part of the plural pixels arranged in a row, a defect signal is generated only in a part of the pixels and does not form a line defect. In such configuration, the bonding material is preferably composed of an X-ray intercepting bonding material for example containing lead, in order that the leaking X-ray from the wavelength converting member does not enter the image pickup elements through the bonding portions of the fiber plates.

In the above-described embodiment, the joint line of the fiber plates is inclined with respect to the pixel row of the image pickup elements in order that the joint line of the fiber plates does not become parallel to the pixel row of the image pickup elements, but it is also possible to adopt the following configuration.

Embodiment 8

Figure 23:
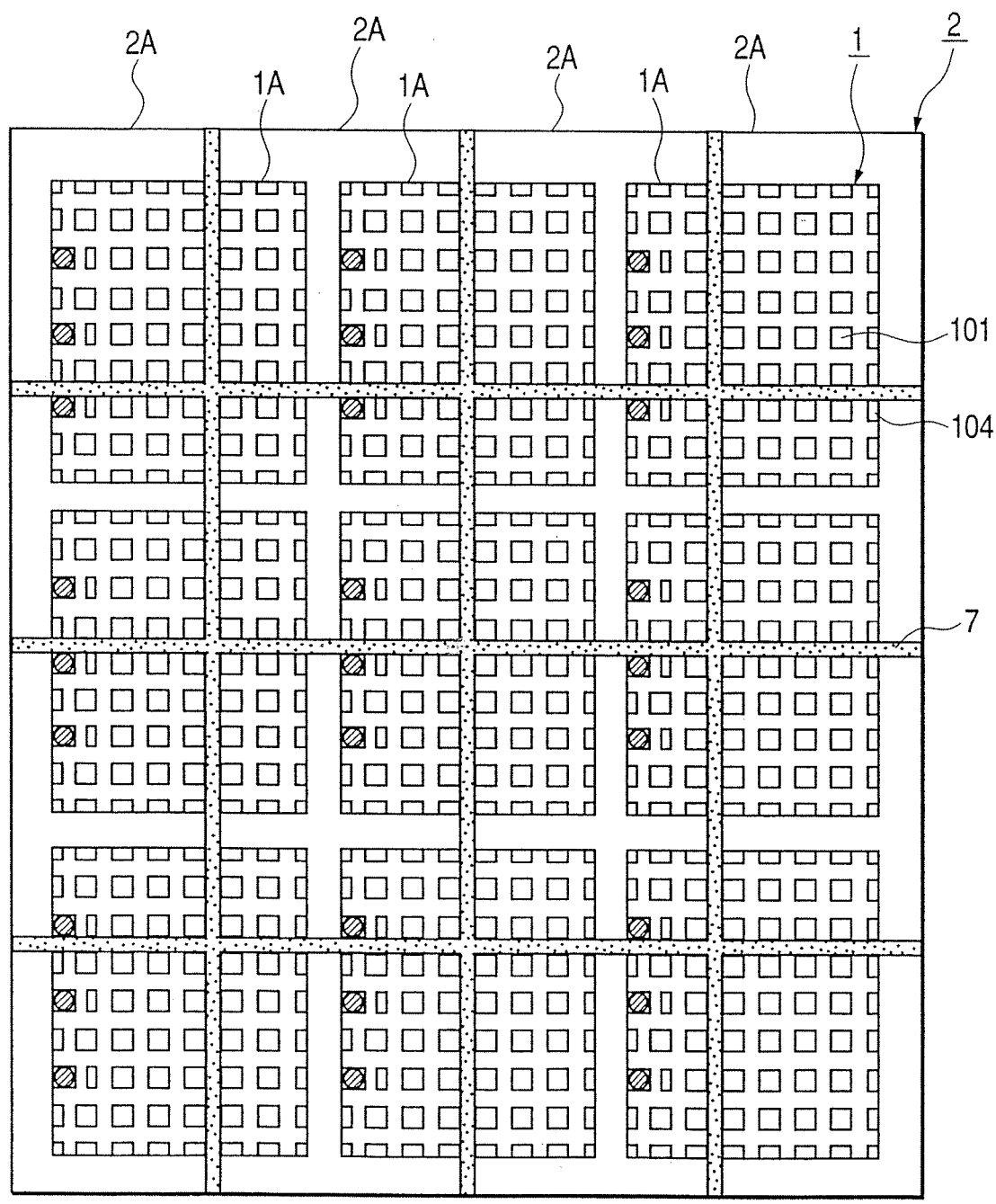
FIG. 23 is a schematic plan view of an X-ray image pickup apparatus constituting still another embodiment of the present invention.
Figure 24:
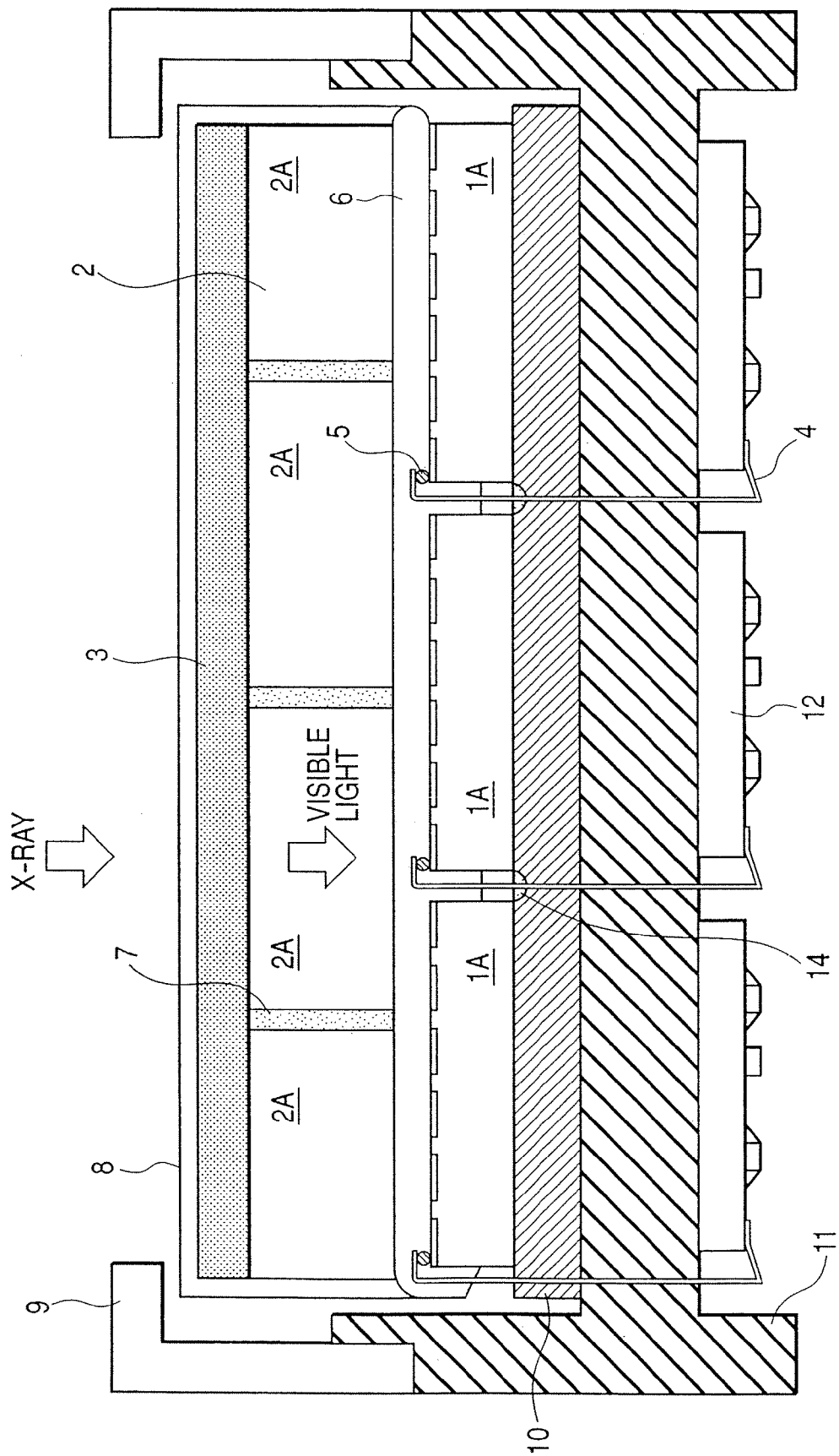
FIG. 24 is a schematic cross-sectional view of the X-ray image pickup apparatus shown in FIG. 23.

FIGS. 23 and 24 are respectively a plan view and a cross-sectional view of another embodiment of the X-ray image pickup apparatus of the present invention.

In the apparatus shown in FIGS. 23 and 24, the joint line of the fiber plates is positioned on the image pickup area of the image pickup element 1A but between the adjacent pixel rows, in order that the light entering from the phosphor through the joints of the bonding portions of the fiber plates does not enter the pixels of the image pickup element. Also, if necessary, the width of the bonding portions 7 (width of joint line) is sufficiently larger than the dimension of the ordinary pixel 104 in order to avoid line defect even if the bonding portion 7 of the fiber plates is somewhat displaced from the gap between the ordinary pixels. In such configuration, the bonding material is preferably composed of an X-ray intercepting bonding material for example containing lead, in order that the X-ray does not enter the image pickup elements through the bonding portions of the fiber plates.

In the configuration shown in FIGS. 23 and 24, there are combined a large-area fiber plate formed by bonding 16 individual fiber plates 2A and a large-area image pickup element composed of nine image pickup element chips 1A, but it is preferable to reduce the dimension of the image pickup element chip thereby selecting the number of the image pickup element chips larger than that of the individual fiber plates.

Embodiment 9

Figure 25:
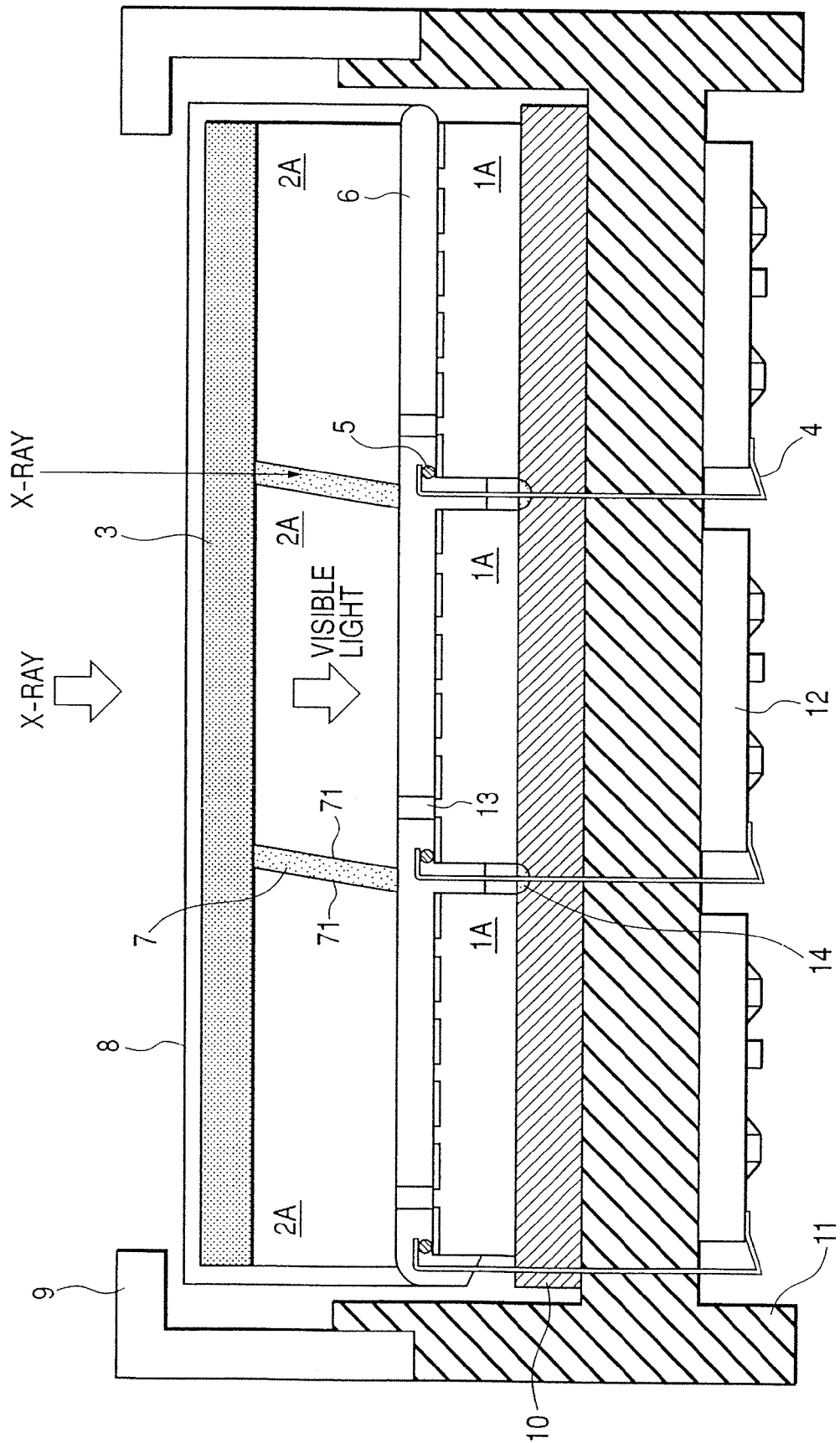
FIGS. 25, 26, 27 and 28 are schematic cross-sectional views of X-ray image pickup apparatuses constituting still another embodiments of the present invention.

FIG. 25 is a schematic cross-sectional view of an embodiment of the X-ray image pickup apparatus of the present invention.

In the fiber plate of this apparatus, the lateral face of the individual fiber plate at the bonding portion thereof is so inclined as to cross the normal line to the light guiding plane.

In the X-ray image pickup apparatus shown in FIG. 25, the end portion (lateral face) of the fiber plate is so formed that the leaking X-ray entering the bonding portion 7 of the fiber plates falls on the lateral face constituting the bonding portion of the fiber plates and does not enter the image pickup element. In order that the leaking X-ray passes the lateral face constituting the bonding portion of the fiber plate, the lateral face 71 of the individual fiber plate 2A can be so formed as to be non-parallel to such leaking X-ray. In the present embodiment, the lateral face 71 of the individual fiber plate is given an inclination of several degrees to several tens of degrees with respect to the normal line to the light guiding plane of the fiber plate, namely with respect to the axes of the optical fibers. In such configuration, the leaking X-ray transmitted by the wavelength converting member 3 enters the fiber plate and intercepted therein, as shown in FIG. 25. Since the X-ray does not enter the image pickup device through the bonding portion of the fiber plate, there can be suppressed the generation of the line-shaped shot noise. The individual fiber plate in this embodiment is composed of a radiation intercepting fiber plate, but the bonding material need not necessarily be composed of a radiation intercepting bonding material.

The bonding material 7 is preferably same as or similar to the fiber plate in the characteristics such as thermal expansion coefficient etc.

In the foregoing, it is assumed that all the lateral faces 71 of the fiber plate have a same inclination to the leaking X-ray, but it is also possible that a part of the lateral faces 71 has such inclination to the leaking X-ray.

Also the apparatus shown in FIG. 25 may have not only a configuration in which the axes of the optical fibers are parallel to the normal line to the light guiding face of the individual fiber plate 2A but also a configuration in which the axes of the optical fibers are parallel to the lateral face of the individual fiber plate 2A. The latter configuration can be realized by preparing plural individual fiber plates formed by cutting a bundle of optical fibers in inclined manner and bonding such individual fiber plates in such a manner that the axes of the optical fibers in such fiber plates become mutually parallel. In such case the position of the light guiding face constituting the light entrance face and that of the light guiding face constituting the light exit face are mutually displaced according to the inclination angle of the optical fibers.

Embodiment 10

Figure 26:
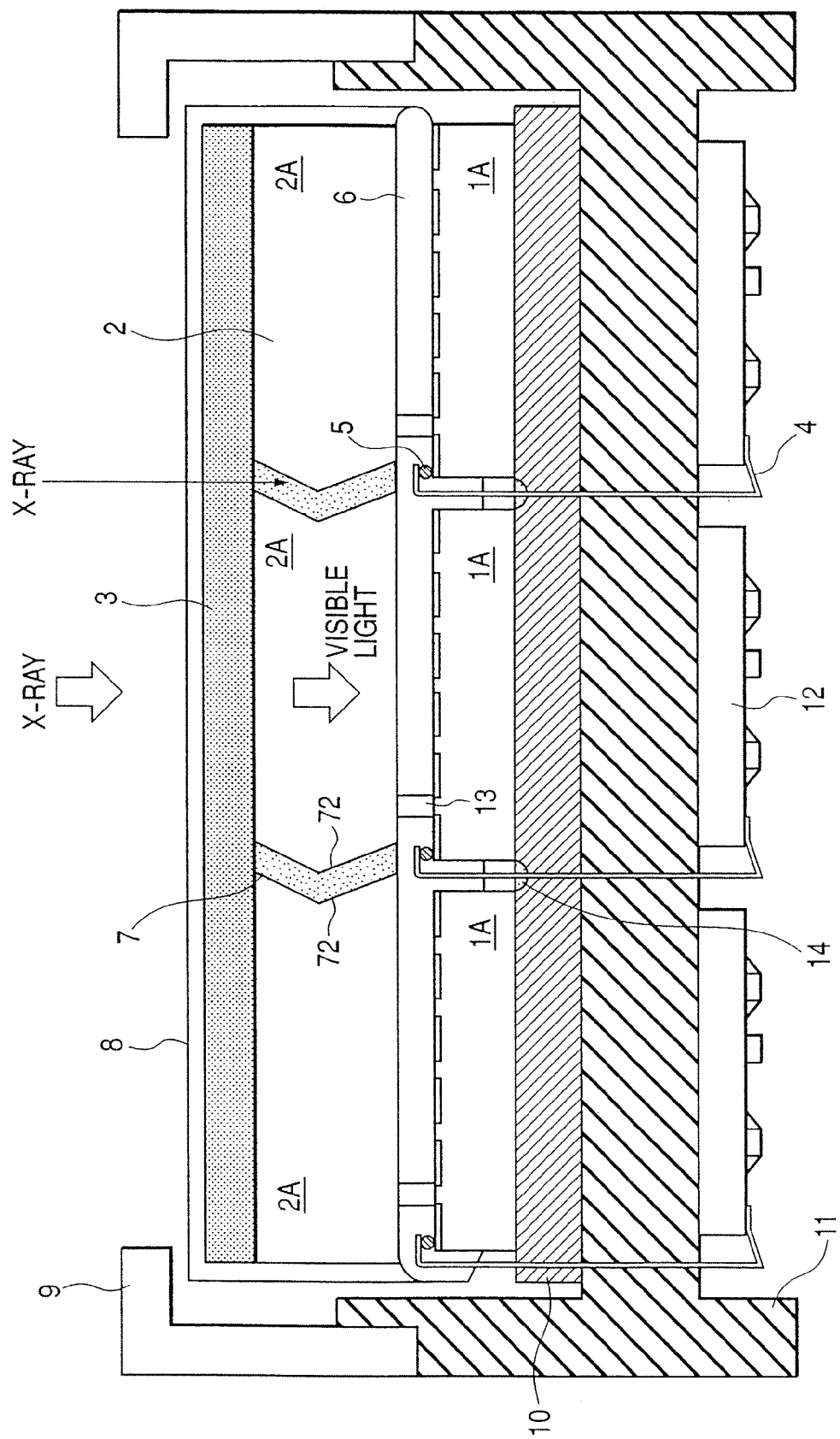

FIG. 26 is a schematic cross-sectional view of an embodiment of the X-ray image pickup apparatus of the present invention.

In the fiber plate of this apparatus, the lateral face constituting the bonding portion of the individual fiber plate is formed as faces inclined across a folding point, both faces crossing the normal line to the light guiding plane.

More specifically, as shown in FIG. 26, the bonding portion 7 of the fiber plate has a chevron shape, so that a part of the lateral face 72 of the fiber plate across the thickness thereof has a certain inclination to the leaking X-ray.

Embodiment 11

Figure 27:
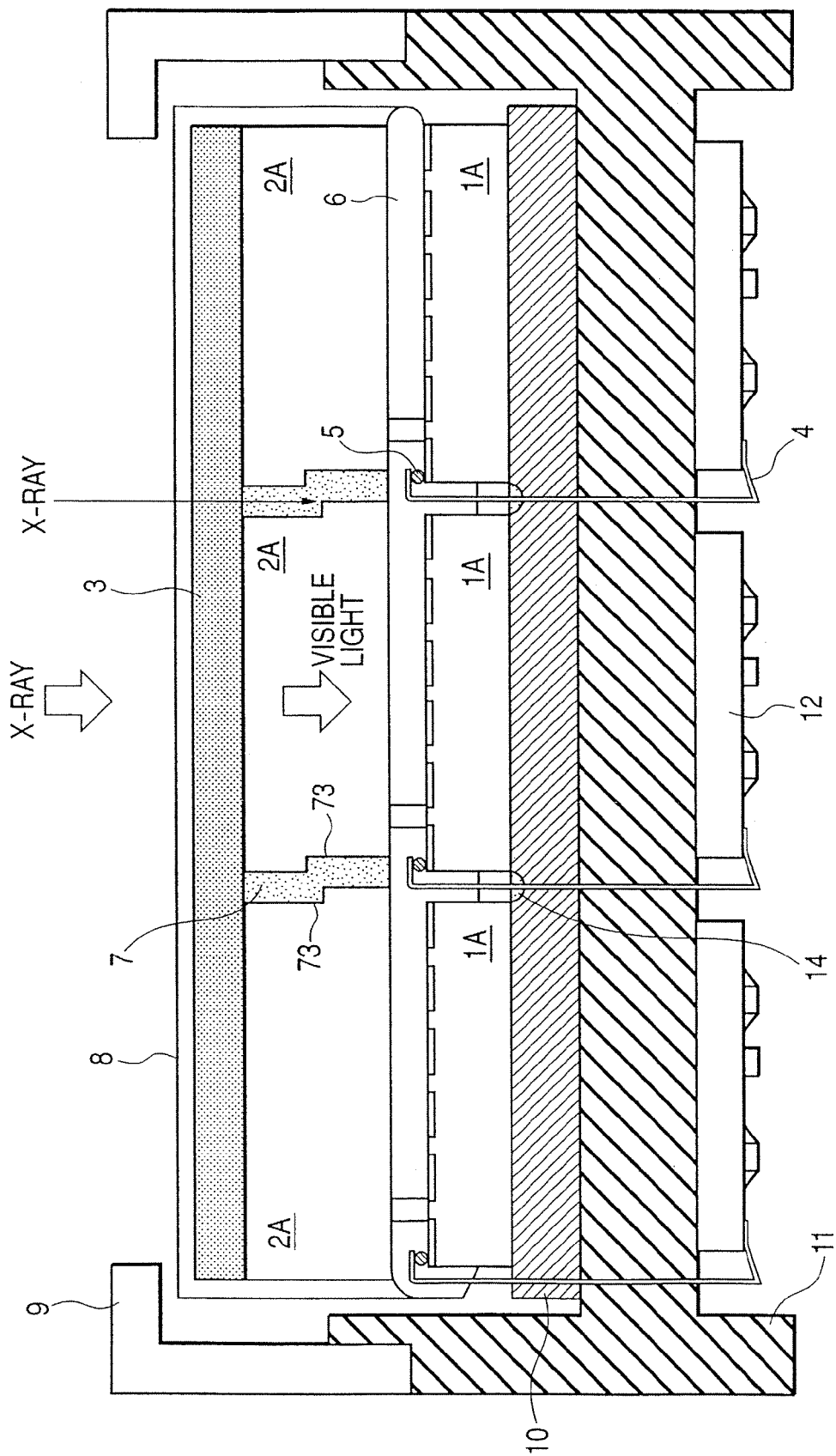

FIG. 27 is a schematic cross-sectional view of an embodiment of the X-ray image pickup apparatus of the present invention.

As shown in FIG. 27, the lateral face of the fiber plate is formed with a step, so that the bonding portion 7 of the fiber plate has a stepped structure. In the fiber plate of this apparatus, the lateral face of the individual fiber plate includes a face crossing the normal line to the light guiding plane, at the above-mentioned step.

In the foregoing there have been explained examples of the shape of the lateral face (bonding portion 7) of the fiber plate to be employed in the present invention.

In summary, the lateral face of the fiber plate to be employed in the present invention can have any other form than those illustrated in the foregoing, such as a zigzag shape or an arc shape, as long as the leaking X-ray entering the bonding portion 7 does not pass through the side of the fiber plate.

Embodiment 12

In case the bonding portion 7 of the fiber plate is positioned above the peripheral pixel of the image pickup element as shown in FIG. 20, since the optical transmittance of the individual fiber plate 2A is different from that of the bonding portion 7 for the individual fiber plates 2A, there will result a line defect covering plural lines if the pixel row of the image pickup element 1 is positioned under such bonding portion 7 and if such bonding portion 7 has a large width. Also if the leaking X-ray, not converted into light but transmitted by the wavelength converting member, enters the image pickup element through the bonding portion, there will result a line-shaped shot noise, thus deteriorating the image quality. The peripheral pixel is made smaller than the ordinary pixel.

Figure 28:
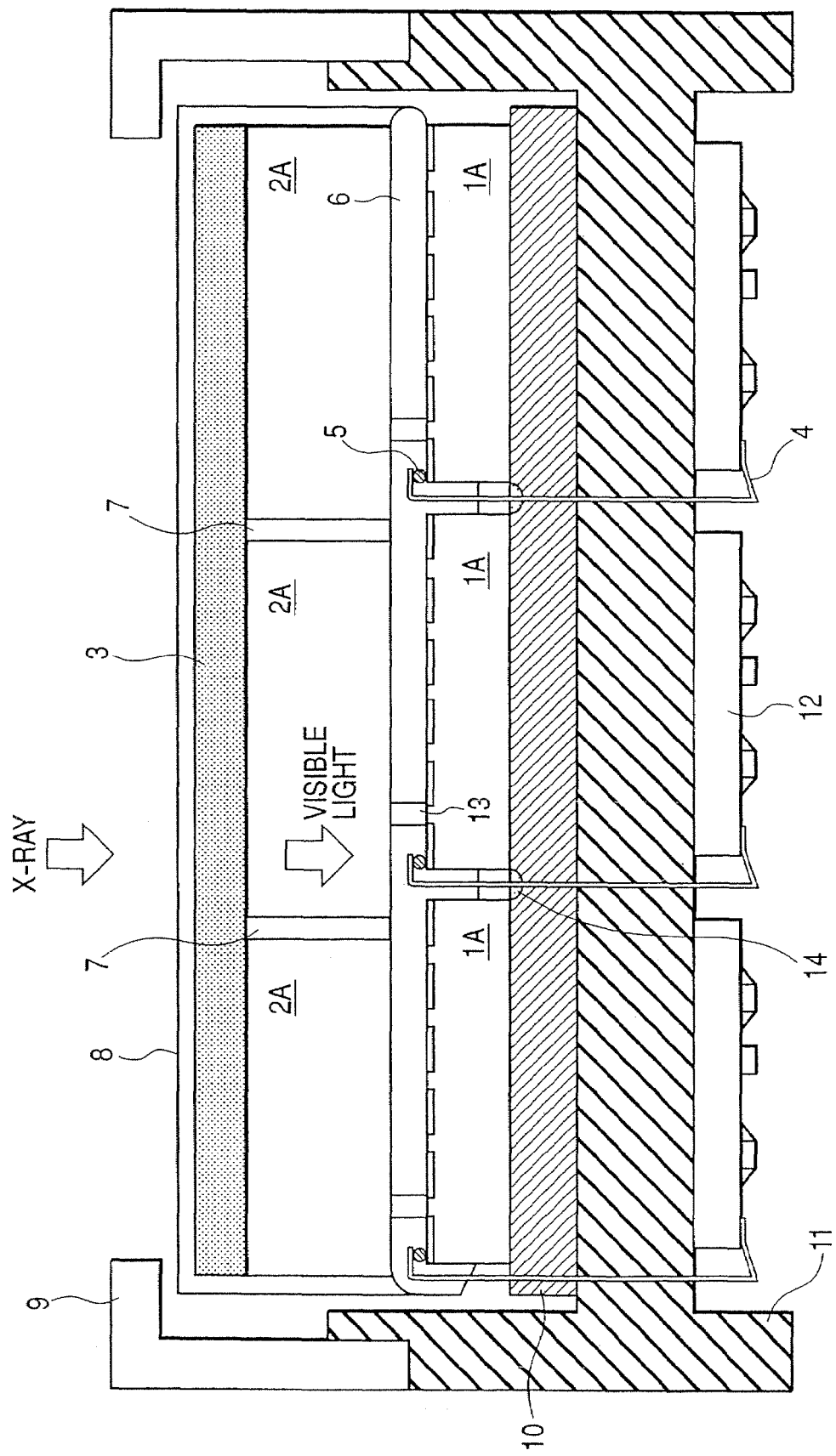
Figure 29:
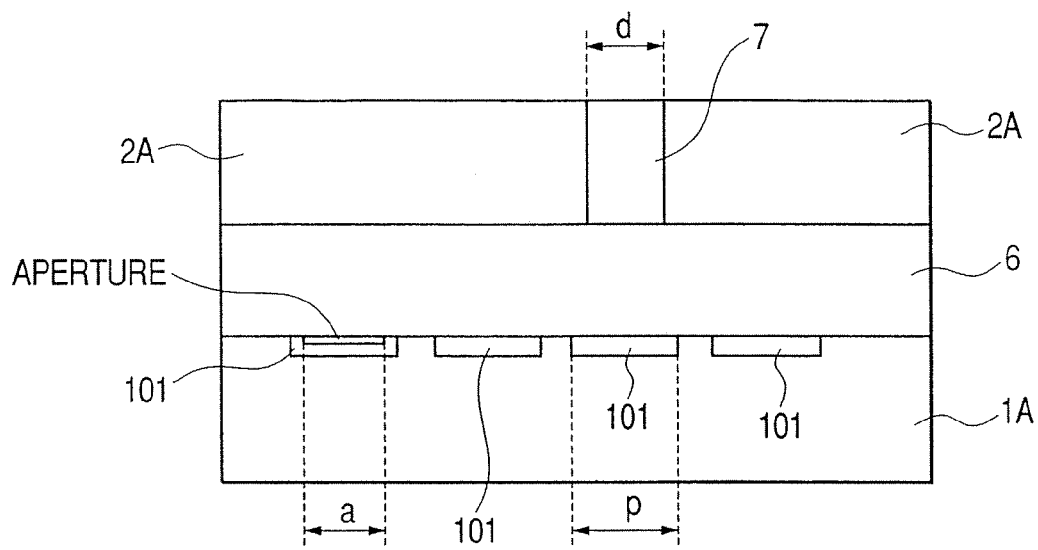
FIG. 29-is a schematic cross-sectional view showing the relationship between a pixel of the image pickup apparatus and a joint portion of the fiber plate in the present invention.

Therefore, in the present embodiment, as shown in FIGS. 28 and 29, the width "d" of the bonding portion 7 of the individual fiber plate is made smaller than the width "P" of the image pickup element 1 (d<P) whereby the line defect is limited to one line even if the pixel row of the image pickup element is positioned under the bonding portion. Also the X-ray leaking from the wavelength converting member 3 can be intercepted by employing a bonding material composed of adhesive containing a radiation intercepting material such as lead. More preferably, the width "d" of the bonding portion 7 is made smaller than the width "a" of an aperture formed by the opaque layer of the pixel 101 (d<a). It is also preferred that the width "d" of the bonding portion 7 of the fiber plate is smaller than the width of the peripheral pixel 101, which is smaller than the width of the ordinary pixel 101, namely that the width "d" of the bonding portion 7 of the fiber plate 2A is smaller than the minimum width of the pixel within the image pickup element 1. The material of the bonding portion is preferably same as or similar to the fiber plate in characteristics such as thermal expansion coefficient.

Embodiment 13

Figure 30:
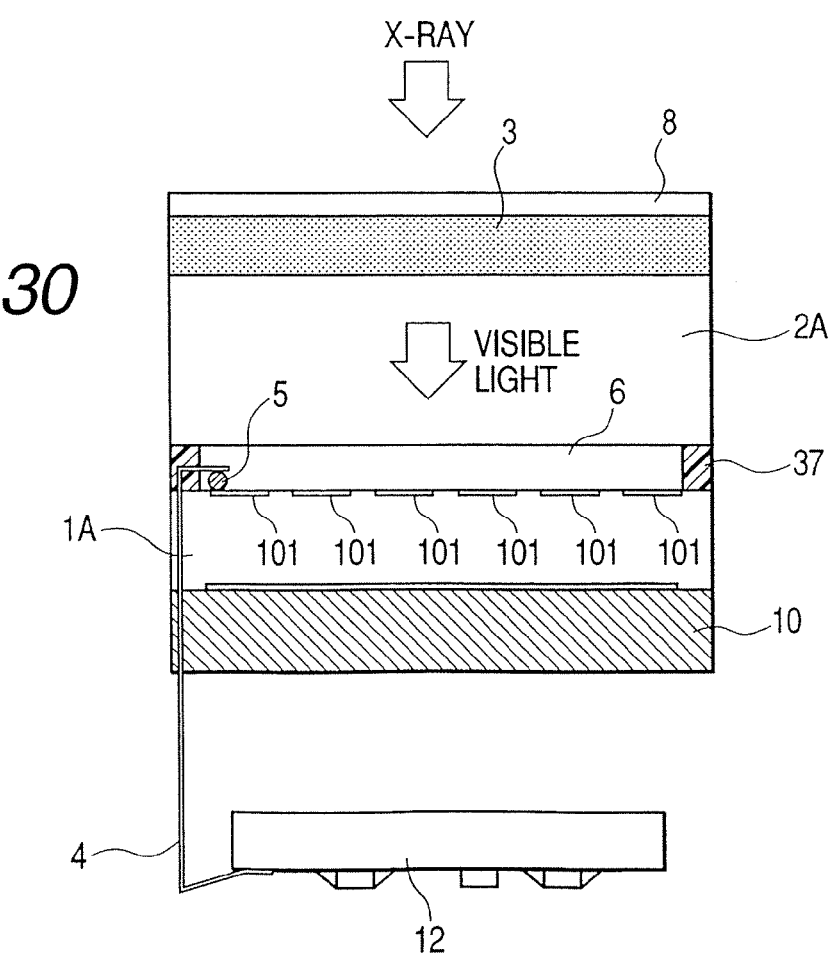
FIG. 30 is a schematic cross-sectional view of an X-ray image pickup apparatus constituting still another embodiment of the present invention.

FIG. 30 is a schematic cross-sectional view of an image pickup unit constituting the X-ray image pickup apparatus in an embodiment of the present invention. The apparatus shown in FIG. 30 is provided with wavelength conversion means 3 for converting X-ray into light of a wavelength detectable with an image pickup element such as visible light, a fiber plate 2A consisting of plural optical fibers for guiding the light, converted by the wavelength conversion means 3, to an image pickup element 1A, a transparent adhesive 6 of excellent elasticity for adhering the fiber plate 2A with an image pickup element 1A having plural pixels 101, an image pickup element 1A having a light-receiving unit for converting the light into an electrical signal, a flexible wiring board 4 having wirings for outputting the electrical signal of the image pickup element 1A to the exterior, a bump 5 for electrically connecting the flexible wiring board 4 with the image pickup element 1A, an aluminum protective sheet 8 for protecting the wavelength converting member 3, a base substrate 10 for mounting the image pickup element 1A, and a seal material 14 for maintaining the transparent adhesive 6 between the fiber plate 2A and the image pickup element 1A.

A large-area image pickup apparatus may be obtained by preparing plural image pickup units as shown in FIG. 30 and bonding lateral faces of neighboring fiber plates 2A so as to provide a large-area radiation receiving surface.

FIGS. 31A to 31D are schematic views showing a producing method for the X-ray image pickup unit, wherein FIGS. 6A and 6C are cross-sectional views while FIGS. 6B and 6D are plan views. The lateral faces of the fiber plate 2A are polished, and the longitudinal and transversal dimensions of the fiber plate 2A are substantially equal to those of the image pickup element 1A whereby they have approximately same areas.

The fiber plate 2A are polished on both surfaces thereof, so that the light guiding face (light entrance/exit face) is composed of a flat polished surface. The polishing method will be explained later.

At first the image pickup element 1A is adhered and fixed to the base substrate 10 with an adhesive 35. On the image taking face of the image pickup element 1A, a spacer 13 of spherical or cylindrical shape is placed in order to maintain the gap between the image pickup element and the fiber plate (FIG. 31A).

Then sealing material 37 is coated on the image pickup element (FIG. 31B). The seal material 37 is provided in a part thereof with an aperture 37A as shown in FIG. 31B. A pixel drive circuit 103 includes vertical shift registers and a horizontal shift register.

Then, after the fiber plate 2A on which the wavelength converting member 3 is formed is positioned on the spacer 13, the fiber plate 2A and the image pickup element 1A are mutually pressed under heating to achieve adhesion (FIG. 31C).

Then, in a vacuum chamber, the gap between each fiber plate 2A and each image pickup element 1A is maintained under a reduced pressure, and an unrepresented port containing the transparent adhesive is attached to the aperture 37A, and the pressure is returned to the atmospheric pressure whereby the transparent adhesive is filled into the gap. Thereafter the aperture 37A is sealed with a sealant 38 (FIG. 31D). The X-ray image pickup unit can be obtained in this manner.

An X-ray image pickup apparatus of a large area can be obtained by arranging and bonding plural X-ray image pickup units in such a manner that the X-ray receiving faces lie on a same plane.

In the example shown in FIGS. 31A to 31D, the seal material 37 is provided only to a position which is inside the end portion of the image pickup element chip 1A by a peripheral pixel, but it may also be provided to the end portion as shown in FIG. 30.

In the present apparatus, the wavelength converting member 3 provided on the light entrance surface of the fiber plate 2A by evaporation, coating or printing, and such process is preferably executed after the polishing of the fiber plate 2. It may also be executed after the fiber plate 2A is adhered to the image pickup element 1A.

Embodiment 14

FIGS. 32A to 32E are schematic views showing another producing method of the X-ray image pickup unit constituting an embodiment of the present invention, wherein FIGS. 32A, 32C and 32D are cross-sectional views while FIGS. 32B and 32E are plan views.

On the image pickup element 1a adhered with the base substrate 10, the spacer 13 is placed in order to maintain the gap between the image pickup element 1A and the fiber plate 2A (FIG. 32A). The fiber plate 2A used herein is in advance planarized by polishing on both surfaces.

Then sealing material 37 is coated on the image pickup element 1 (FIG. 32B). The seal material 37 is provided, as shown in FIG. 32B, in a part thereof with an aperture 37A, through which transparent adhesive is filled by a vacuum injection method as will be explained later.

Then, the fiber plate 2A is positioned on the spacer 13 and adhered (FIG. 32C). Then, in a vacuum chamber, the gap between the fiber plate 2A and the image pickup element 1A is maintained under a reduced pressure, and a port containing the transparent adhesive is attached to the aperture 37A, and the pressure is returned to the atmospheric pressure whereby the transparent adhesive 6 is filled into the gap. Thereafter the aperture 37A is sealed with the sealant 38. Then the fiber plate 2A is polished to the area of the image pickup element 1A and the fiber plate 2A and the image pickup element chip 1A are mutually so aligned that the lateral faces thereof coplanarly match (FIG. 31D). The polishing in this step is not chemical polishing utilizing polishing solution such as potassium hydroxide, ammonia or hydrogen peroxide water, but is executed by mechanical polishing in order to prevent damage to the image pickup element 1A.

On the fiber plate 2A, a phosphor constituting the wavelength converting member 3 of an area same as that of the fiber plate 2A is adhered, or a phosphor of a larger area is adhered and is cut into the size of the fiber plate 2A. An X-ray image pickup unit as shown in FIG. 32E can be obtained in this manner.

An X-ray image pickup apparatus of a large area can be obtained by arranging and bonding plural X-ray image pickup units in such a manner that the X-ray receiving faces lie on a same plane.

Embodiment 15

FIGS. 33A to 33F are schematic views showing a producing method for the large-area fiber plate constituting an embodiment of the present invention.

Figure 33D:
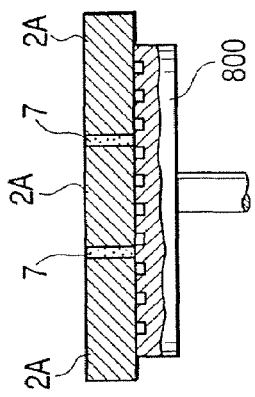
FIGS. 33A, 33B, 33C, 33D, 33E and 33F are schematic views showing a method producing a fiber plate in an embodiment of the present invention.
Figure 33E:
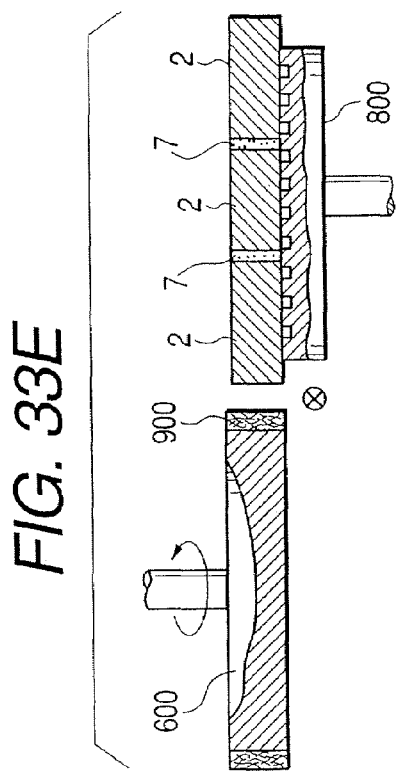
Figure 33F:
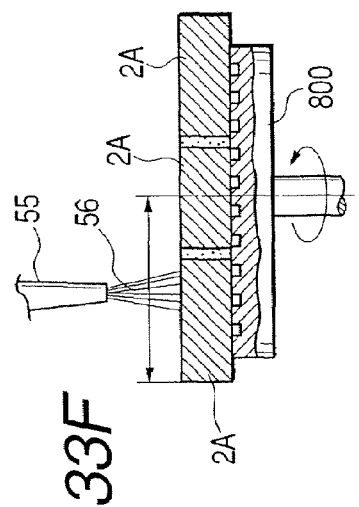
Figure 33A:
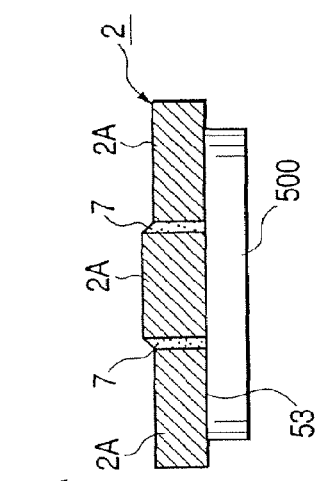

At first plural individual fiber plates 2A are placed on an adhering stage 500, and the bonding material 7 is filled between the fiber plates 2A for example with a dispenser. In this operation, the adhering stage 500 constitutes a reference plane 53 for the fiber plates 2A (FIG. 33A).

Figure 33B:
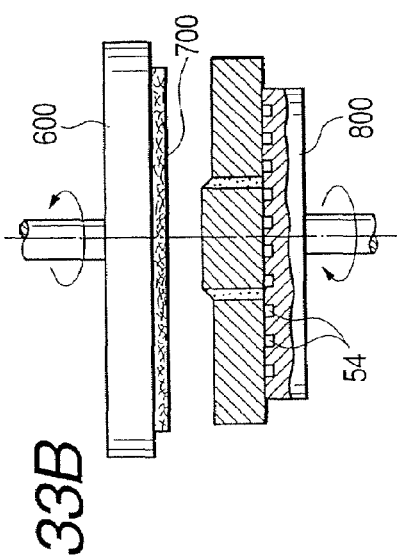

After the setting of the adhesive used as the bonding material 7, the bonded large-area fiber plate 2 is placed on a polishing stage 800 with the reference plane 53 at the side of a suction hole 54. A polishing pad 700 composed for example of felt is mounted on a polishing disk 600 (FIG. 33B).

Figure 33C:
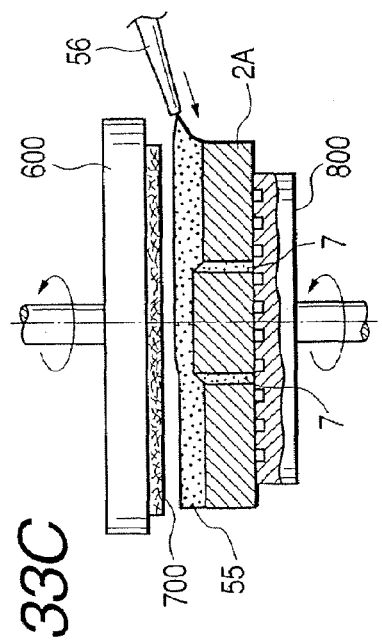

Polishing agent 55 is poured onto the large-area fiber plate 2 and the bonding portion 7 and the polishing disk 600 and the polishing stage 800 are rotated in mutually opposite directions under pressurized contact, thereby polishing the individual fiber plates 2A and the bonding portion 7 (FIG. 33C). The polishing agent can be so-called slurry containing grinding particles of silica, celia or alumina family in liquid consisting of at least one of water and aqueous solution of potassium hydroxide, ammonia and hydrogen peroxide. In this manner there can be obtained the large-area fiber plate 2 which is so planarized that the individual fiber plates 2A and the bonding portion 7 lie on a same plane (FIG. 33D).

Then polishing felt 900 is mounted on the external periphery of the polishing disk 600, and such polishing disk is pressed under rotation to the lateral face of the large-area fiber plate 2 and the polishing stage 800 is moved from the front side to the rear side of the drawing (FIG. 33E), thereby polishing the lateral face of the large-area fiber plate 2. Subsequently, the polished surface is spin rinsed with rinsing liquid 56 supplied for example from a spray nozzle 55, and the polishing stage 800 is then rotated at a high speed to dry the fiber plates 2A and the bonding portion 7.

If necessary, the reference plane side may also be polished similarly to obtain the large-area fiber plate with polished light guiding faces.

Embodiment 16

Figure 34:
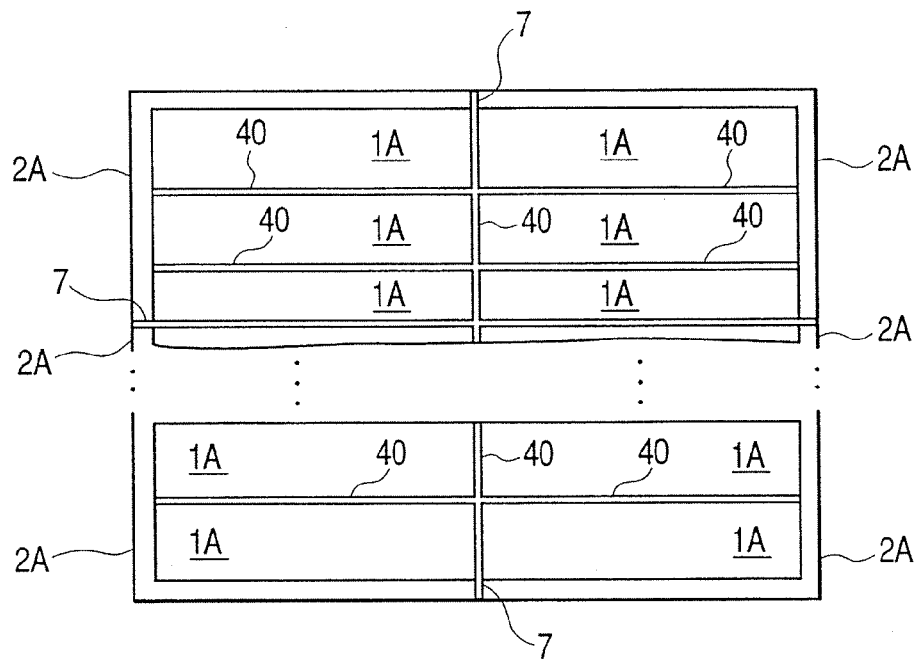
FIG. 34 is a schematic plan view of a radiation image pickup apparatus in another embodiment of the present invention.

FIG. 34 is a plan view showing an embodiment of the radiation image pickup apparatus of the present invention.

The radiation image pickup apparatus of the present embodiment is provided with a large-area fiber plate prepared by arranging for example ten rectangular (60×150 mm) individual fiber plates 2A in two columns by five rows and a large-area image pickup element prepared by arranging 28 rectangular (20×143 mm) image pickup element chips 1A in two columns by 14 rows.

The large area fiber plate and the large-area image pickup element are so assembled that the bonding portion 7 between the left and right individual fiber plates 2A in FIG. 34 is positioned on the gap between the left and right image pickup element chips 1A. On the other hand, as shown in FIG. 34, the bonding portion 7 between the vertically adjacent individual fiber plates 2A does not particularly match the gap between the vertically adjacent image pickup element chips 1A. If necessary, it is preferred to select the width of the bonding portion 7 (width of joint line) at least between the vertically adjacent individual fiber plates 2A smaller than the width of the pixels of the image pickup element chips 1A.

Also by arranging the image pickup element chips 1A in two columns or two rows as shown in FIG. 34, the external connection terminals of all the image pickup element chips 1A can be positioned not between the chips but on a free end (one of the four sides of the large-area image pickup element). In this manner it is possible to further reduce the gap between the adjacent image pickup element chips.

Among the image pickup apparatuses explained in the foregoing, the apparatus obtained by bonding plural fiber plates 2A with adhesive to obtain a large-size fiber plate, then adhering the base substrate mounting plural frame-free image pickup elements on such large-size fiber plate and combining such assembly with the wavelength converting member can provide the following advantages:

1) a large-area detecting apparatus can be prepared;
2) an inexpensive large-area fiber plate can be prepared;
3) a high efficiency of light utilization can be achieved since the fibers are not bent nor inclined;
4) the fiber plate can be prepared with a minimum thickness;
5) the sensor need not be matched with the shape of the fiber plate;
6) the large-area fiber plate can be prepared easily; and
7) wavelength converting member often showing uneven growth, such as alkali metal halide can be satisfactorily grown, so that the obtained image provides satisfactory image quality with reduced unevenness.

Based on these advantages, there can be provided an X-ray image pickup apparatus which is capable of providing moving X-ray image, excellent in image quality, thin, highly reliable and having a large image input area. In addition the apparatus is inexpensive.

[Radiation Image Pickup System]

In the following there will be explained a radiation image pickup system utilizing the image pickup apparatus of the foregoing embodiments.

Figure 35:
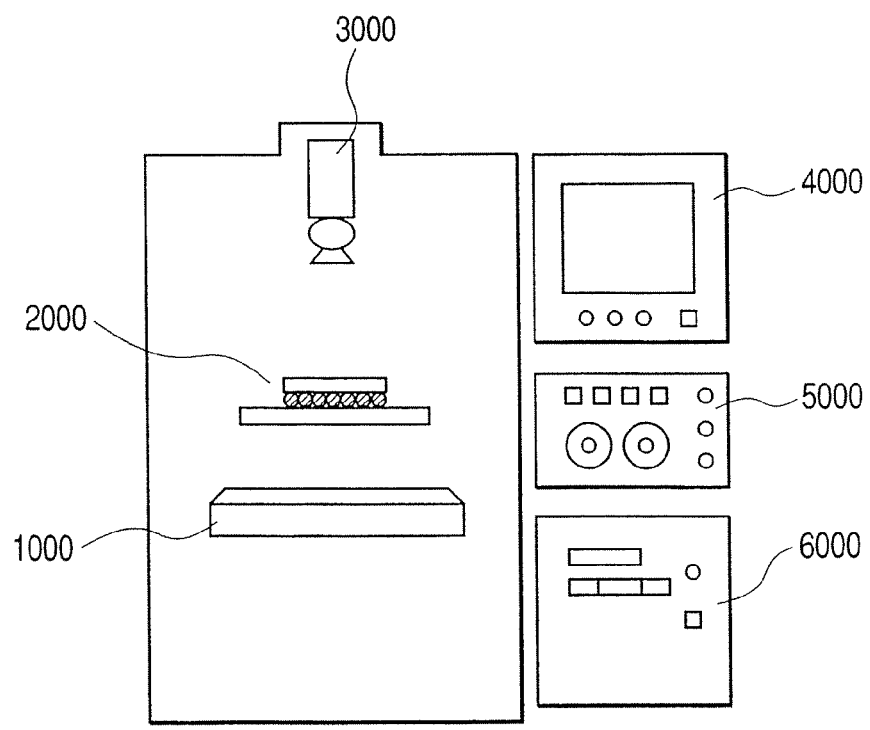
FIG. 35 is a schematic view showing the configuration of a non-destructive testing system provided with an X-ray image pickup apparatus of the present invention.

FIG. 35 is a schematic view showing the concept of a non-destructive testing system provided with an X-ray image pickup apparatus of the foregoing embodiments.

In FIG. 35, there are shown an X-ray image pickup apparatus 1000 of the foregoing embodiments, an object 2000 of the non-destructive testing, for example an article to be incorporated in an electric equipment, a microfocus X-ray generator 3000 constituting a radiation source for irradiating the object 2000 with X-ray, an image processing apparatus 6000 for processing the signal from the X-ray image pickup apparatus 1000, a monitor 4000 for displaying an image processed by the image processing apparatus 6000, and a controller 5000 for controlling the image processing apparatus 6000 and the monitor 4000.

In the non-destructive testing system shown in FIG. 35, the object 2000 to be tested is irradiated by the X-ray generated by the microfocus X-ray generator 3000, and the defect inside the object 2000 is outputted through the X-ray image pickup apparatus 1000 to the image processing apparatus 6000, which processes the image signals of the peripheral pixels of each of the aforementioned image pickup element 1, eventually with dark signal correction, to display an image on the monitor 4000.

The image displayed on the monitor 4000 can be subjected for example to image enlargement or reduction or density control under the instruction of the controller 5000. Through the image displayed on the monitor 4000, the defect inside the object 2000 can be inspected. If no defect is found in the object 2000, it is considered satisfactory and is used for assembling in the electrical equipment. If a defect is found in the object 2000, it is identified damaged and is removed from the manufacturing line.

Figure 36:
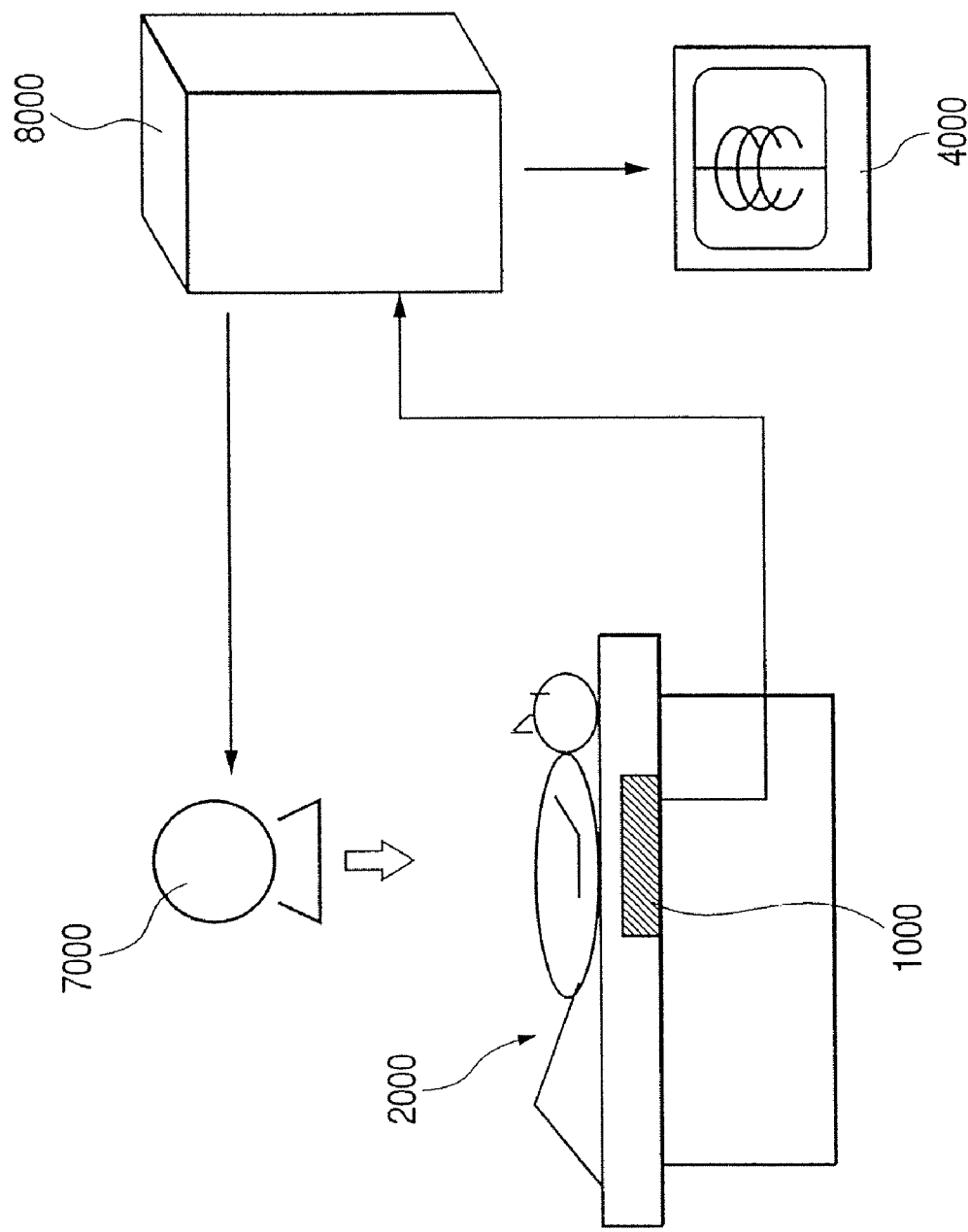
FIG. 36 is a schematic view showing the configuration of an X-ray diagnostic system provided with an X-ray image pickup apparatus of the present invention.
Figure 37:
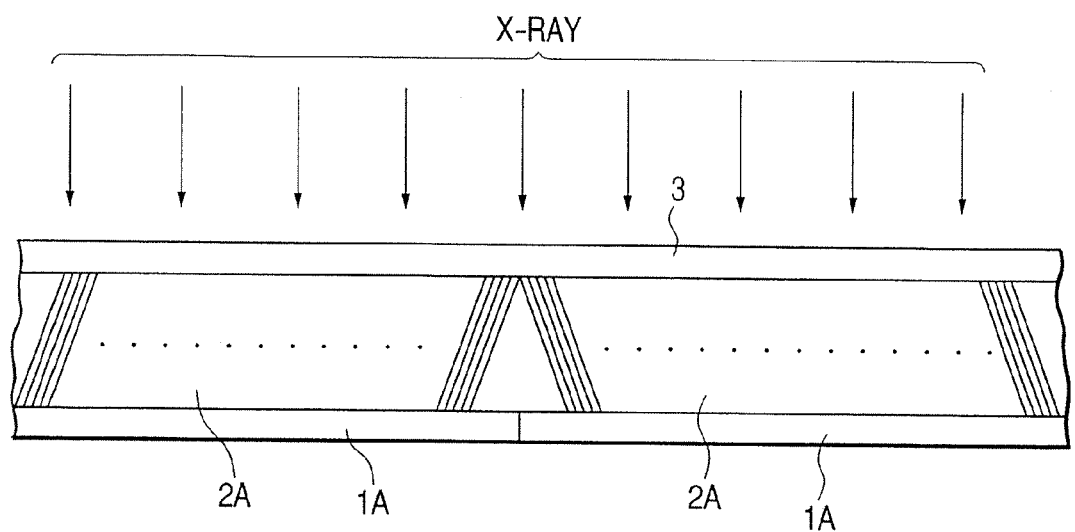
FIG. 37 is a schematic cross-sectional view of an image pickup apparatus employing a conventional large-area fiber plate.
Figure 38:
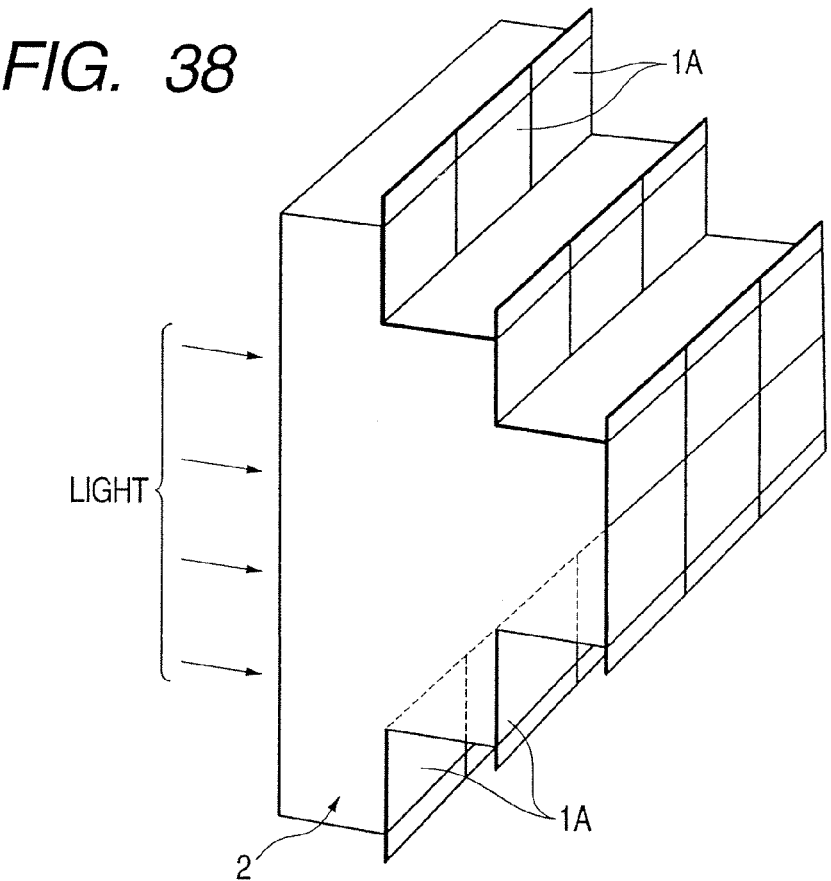
FIG. 38 is a schematic cross-sectional view of an image pickup apparatus employing another conventional large-area fiber plate.

FIG. 36 is a schematic view showing the concept of an X-ray diagnostic system provided with an X-ray image pickup apparatus of the foregoing embodiments.

In FIG. 36, there are shown a bed provided with an X-ray image pickup apparatus 1000, an X-ray generator 7000 constituting a radiation source for irradiating an object 2000 with X-ray, an image processor 8000 for processing the signal from the X-ray image pickup apparatus 1000 and controlling the irradiation time of X-ray from the X-ray generator 7000, and a monitor 4000 for displaying an image processed by the image processor 8000. In FIG. 36, components equivalent to those in FIG. 35 are represented by corresponding numbers.

In the X-ray diagnostic system shown in FIG. 36, the X-ray generator 7000 generates X-ray according to the instruction from the image processor 8000 to irradiate the object 2000 on the bend, whereby the Roentgen information of the object 2000 is outputted through the X-ray image pickup apparatus 1000 to the image processor 8000, which processes the image signals of the peripheral pixels of each of the aforementioned image pickup element 1, eventually with dark signal correction, to store an image in an unrepresented memory or to display an image on the monitor 4000.

The image displayed on the monitor 4000 can be subjected for example to image enlargement or reduction or density control under the instruction of the image processor 8000. Through the image displayed on the monitor 4000, the doctor diagnoses the object 2000.

The information of the object, after the diagnosis by the doctor, may be recorded for example in a floppy disk, by recording means provided in this system.

In the foregoing embodiments, there have been explained cases of utilizing X-ray, but the present invention is likewise applicable to other radiations such as α-ray, β-ray or γ-ray. Also the light is an electromagnetic wave of a wavelength range detectable by the pixel and includes visible light. The present invention is furthermore applicable to a converting apparatus for converting an electromagnetic wave, including radiation, into an electrical signal.

The invention claimed is:

1. A radiation imaging apparatus comprising:
a photoelectric conversion device for converting light into an electric signal, wherein the photoelectric conversion element comprises a plurality of photoelectric conversion device chips arranged on a substrate, and each photoelectric conversion device chip comprises a plurality of pixels;
a wavelength converter for converting radiation into light which can be sensed by the photoelectric conversion device; and
a fiber plate disposed between the wavelength converter and the photoelectric conversion device, wherein the fiber plate comprises a plurality of individual fiber plates of the same thickness arranged adjacently side by side, each of the individual fiber plates comprising a group of optical fibers having parallel axes, wherein the plurality of individual fiber plates are bonded together at lateral faces thereof so that the axes of the optical fibers of the individual fiber plates are parallel to each other, and wherein the fiber plate and the plurality of photoelectric conversion device chips are mutually adhered by a transparent adhesive.

2. The radiation imaging apparatus according to claim 1, wherein
the axes of said optical fibers are parallel to, or at an incline with, the line normal to the light guiding plane.

3. The radiation imaging apparatus according to claim 1, wherein at least one of the light guiding plane and the lateral faces of said optical fibers is a polished surface.

4. The radiation imaging apparatus according to claim 1, wherein
said lateral faces are mutually bonded by at least either of an adhesive material or a metal.

5. The radiation imaging apparatus according to claim 1, wherein
the bonding portion between the plurality of individual fiber plates is a radiation shielding bonding portion.

6. The radiation imaging apparatus according to claim 1, wherein said fiber plate disposed between the wavelength converter and the photoelectric conversion device has a radiation shielding property, and each lateral face has a plane crossing a line normal to a light guiding plane of the individual fiber plate.

7. The radiation imaging apparatus according to claim 1, wherein
a width of a gap between the adjacent individual fiber plates is smaller than a width of a said pixel of the photoelectric conversion device.

8. The radiation imaging apparatus according to claim 1, wherein
the plurality of pixels have light receiving areas which are mutually different, and a width of a gap between the individual fiber plates adjacent to each other is smaller than a width of a said pixel of a smallest light receiving area.

9. The radiation imaging apparatus according to claim 1, wherein
a gap between the individual fiber plates adjacent to each other is disposed over a gap between the photoelectric conversion device chips adjacent to each other.

10. The radiation imaging apparatus according to claim 1, wherein
a gap between the individual fiber plates adjacent to each other is disposed over an effective pixel area of the photoelectric conversion device chip.

11. The radiation imaging apparatus according to claim 1, wherein
a gap between the individual fiber plates adjacent to each other is disposed over a gap between the pixels.

12. The radiation imaging apparatus according to claim 1, wherein
a bonding line along a gap between the individual fiber plates adjacent to each other crosses, at an angle of 0-90 degree, a bonding line along a gap between the photoelectric conversion device chips adjacent to each other.

13. The radiation imaging apparatus according to claim 1, wherein
front and rear faces as the light guiding faces of the fiber plate have the same area.

14. The radiation imaging apparatus according to claim 1, wherein
the photoelectric conversion device chip and the individual fiber plate have substantially the same size.

* * * * *

UNITED STATES PATENT AND TRADEMARK OFFICE
CERTIFICATE OF CORRECTION

PATENT NO. : 7,377,701 B2
APPLICATION NO. : 11/767347
DATED : May 27, 2008
INVENTOR(S) : Kenji Kajiwara et al.

It is certified that error appears in the above-identified patent and that said Letters Patent is hereby corrected as shown below:

<u>COLUMN 1</u>:

Line 17, "therefore" should read --therefor--.

<u>COLUMN 3</u>:

Line 23, "are" should read --is--.

<u>COLUMN 4</u>:

Line 38, "plate" should read --plates--.

<u>COLUMN 7</u>:

Line 25, "29-is" should read --29 is--.

<u>COLUMN 10</u>:

Line 21, "and the end chipping" should read --at the end--.

<u>COLUMN 16</u>:

Line 9, "is" should read --are--.

<u>COLUMN 20</u>:

Line 38, "are" should read --is--.

UNITED STATES PATENT AND TRADEMARK OFFICE
CERTIFICATE OF CORRECTION

PATENT NO.       : 7,377,701 B2
APPLICATION NO.  : 11/767347
DATED            : May 27, 2008
INVENTOR(S)      : Kenji Kajiwara et al.

It is certified that error appears in the above-identified patent and that said Letters Patent is hereby corrected as shown below:

COLUMN 26:

Line 17, "degree," should read --degrees,--.

Signed and Sealed this

Twenty-eighth Day of October, 2008

JON W. DUDAS
*Director of the United States Patent and Trademark Office*